US010233484B2

(12) United States Patent
Anderson et al.

(10) Patent No.: US 10,233,484 B2
(45) Date of Patent: Mar. 19, 2019

(54) METHODS AND SYSTEMS FOR RAPID DETECTION OF MICROORGANISMS USING FREE ANTIBODIES

(71) Applicant: Laboratory Corporation of America Holdings, Burlington, NC (US)

(72) Inventors: Dwight Lyman Anderson, Minneapolis, MN (US); Ben Barrett Hopkins, Sherman Oaks, CA (US); Jose S. Gil, Winnetka, CA (US); Stephen Erickson, White Bear Township, MN (US); Ekaterina Kovacheva, Gardena, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 14/625,515

(22) Filed: Feb. 18, 2015

(65) Prior Publication Data

US 2015/0233918 A1    Aug. 20, 2015

Related U.S. Application Data

(60) Provisional application No. 61/940,968, filed on Feb. 18, 2014.

(51) Int. Cl.
*C12Q 1/24* (2006.01)
*C12Q 1/04* (2006.01)

(52) U.S. Cl.
CPC .................. *C12Q 1/24* (2013.01); *C12Q 1/04* (2013.01); *G01N 2469/10* (2013.01)

(58) Field of Classification Search
CPC .......... A61K 2039/505; A61K 2300/00; C07K 16/1289; C07K 2317/55; C12Q 1/6897; C12Q 2565/201; C12Q 2600/136; C12N 15/1037; C40B 40/02; C40B 30/04; G01N 2500/02
See application file for complete search history.

(56) References Cited

U.S. PATENT DOCUMENTS

| | | | |
|---|---|---|---|
| 7,282,345 B1 * | 10/2007 | Hancock | G01N 33/5748 435/7.23 |
| 2004/0137430 A1 | 7/2004 | Anderson et al. | |
| 2006/0024710 A1 | 2/2006 | Weiss et al. | |
| 2006/0094076 A1 | 5/2006 | Stave et al. | |
| 2009/0246752 A1 | 10/2009 | Voorhees et al. | |
| 2010/0291541 A1 | 11/2010 | Evoy et al. | |
| 2011/0201013 A1 | 8/2011 | Moore | |
| 2013/0122549 A1 | 5/2013 | Lu et al. | |
| 2013/0216997 A1 | 8/2013 | Anderson et al. | |

FOREIGN PATENT DOCUMENTS

| | | |
|---|---|---|
| JP | S61215947 | 9/1986 |
| JP | S6312960 | 1/1988 |
| JP | H0251063 | 2/1990 |
| JP | 2006509514 | 3/2006 |

OTHER PUBLICATIONS

Gonzalez et al. J. Appl. Bacteriol. 1993, vol. 74 (4). pp. 394-401.*
Gutierrez et al. (B) Journal of Food Protection, 1994, No. 8, pp. 658-752.*
Abacm plc 1998-2016.*
Myyrylainen et al. Journal of Nanobiotechnology, Nov. 26, 2010, pp. 1-6.*
Wu et al. FEMS Yeast Research, 2007, (7), pp. 465-470.*
Radoseve et al. Journal of Immunologist Methods 2003, vol. 272, Issue 1-2, pp. 219-233.*
Ingram et al. Clinical and Diagnostic Laboratory Immunology, 1998, vol. 5(40, pp. 567-573.*
Gutierrez et al. (A) Journal of Food Protection, 1997, vol. 1, pp. 23-27.*
Sudhir Paul , Section 3.14. Screening for L-Chain Expression by Enzyme-Linked Immunoflow Assay (ELIFA), p. 389 of Antibody Engineering Protocols. Edited by Sudhir Paul, 1995, Humana Press Inc. 9999 Riverview Drive, Suite 208, Totowa, New Jersey 07512.*
Itoh et al. Bio Phar. Bull.2002, vol. 25, No. 8, pp. 986-990.*
Sudhir in Section 3.15. ELIFA for screening of the libraries for antigen binding (See Note 16) p. 392) in Antibody Engineering Protocols. Edited by Sudhir Paul, 1995, Humana Press Inc.*
Bague, J., Detection of Recombinant Human Erythropoietin and Analogues through Immunorecognition and N-Giycolyi-Neuraminic Acid Identification, Doctoral Thesis Pompeu Fabra University, Department of Experimental and Health Sciences, 2011, Retrieved from http://www.tesisenred.net/bitstream/handle/10803/31969/tjm.pdf?sequence=1 as available via the Internet and printed Mar. 27, 2013.
PCT/US13/27155, "International Search Report and Written Opinion" dated May 6, 2013.
PCT/US13/27060, "International Search Report and Written Opinion" dated Apr. 29, 2013.
U.S. Appl. No. 13/772,887, Restriction Requirement dated Dec. 31, 2013.
European Patent Office, Extended European Search Report, European Application No. 13751965 dated Sep. 30, 2015.
Galikowska et al., Specific detection of *Salmonella enterica* and *Escherichia coli* strains by using ELISA with bacteriophages as recognition agents, Eur. J. Clin. Microbiol. Infect. Dis., 2011, 30(9):1067-73.

(Continued)

*Primary Examiner* — Bao Q Li
(74) *Attorney, Agent, or Firm* — Kilpatrick Townsend & Stockton LLP

(57) ABSTRACT

Disclosed herein are methods and systems for detection of a microorganism of interest using an amplification assay. The methods and systems utilize the specificity of binding agents, such as antibodies, to rapidly detect low levels of a specific microorganism present in a sample. In certain embodiments, antibodies are bound to a large number of the available binding sites on a microorganism.

16 Claims, 10 Drawing Sheets

(56) References Cited

OTHER PUBLICATIONS

Goodridge, L. et al., Reporter bacteriophage assays as a means to detect foodborne pathogenic bacteria, Food research International, 2002, 35:863-870.
Gutiérrez et al., Monoclonal antibodies and an indirect ELISA for detection of psychrotrophic bacteria in refrigerated milk, J. Food. Prot., 1997, 60(1):23-7.
Hagens, S. et al., Bacteriophage for Biocontrol of foodborne pathogens: calculations and considerations, Curr. Pharm. Biotechnol., 2010, 11(1):58-68.
Kim et al., Dipstick immunoassay to detect enterohemorrhagic *Escherichia coli* O157:H7 in retail ground beef, Appl. Environ. Microbiol., 1992, 58(5):1764-7.
Noguera, P. et al., Carbon nanoparticles in lateral flow methods to detect genes encoding virulence factors of Shiga toxin-producing, Anal Bioanal. Chem., 2011, 399(2): 831-838.
Patent Cooperation Treaty, International Search Report and Written Opinion, International Application No. PCT/US2015/016430, dated Aug. 14, 2015.
Rees, C. et al., Chapter 14—The use of phage detection, antibiotic sensitivity testing and enumeration, In: Understanding Tuberculosis—Global Experiences and Innovative Approaches to the Diagnosis, 2012, Intech, Edited by Dr. Pere-Joan Cardona.
Smietana, M. et al., Detection of bacteria using bacteriophages as recognition elements immobilized on long-period fiber gratings, Opt Express., 2011, 19(9):7971-8.
Ulitzur, N. et al., New rapid and simple methods for detection of bacteria and determination of their antibiotic susceptibility by using phage mutants, Appl. Environ. Microbiol., 2006, 72(12):7455-7459.
EP 15706660.6, "Communication Pursuant to Rule 164(2)(b) and Article 94(3) EPC", dated Nov. 13, 2017, 4 pages.
Hoszowski et al., "Rapid detection and enumeration of *Salmonella* in chicken carcass rinses using filtration, enrichment and colony blot immunoassay", International Journal of Food Microbiology, vol. 28, No. 1, Jan. 1, 1996, pp. 341-350, 10 pages.
Mai et al., "Rapid detection of trace bacteria in biofluids using porous monoliths in microchannels", Biosensors and Bioelectronics, vol. 54, Nov. 12, 2013, pp. 435-441, 7 pages.
Mazenko et al., "Filtration capture immunoassay for bacteria: optimization and potential for urinalysis", Journal of Microbiological Methods, vol. 36, No. 1, Jun. 1999, pp. 157-165, 9 pages.
Tortorello et al., "Antibody-direct epifluorescent Filter technique for rapid, direct enumeration of *Escherichia coli* 0157:H7 in beef", Applied and Environmental Microbiology, vol. 60, No. 1, Oct. 1, 1994, pp. 3553-3559, 7 pages.

\* cited by examiner

1

METHODS AND SYSTEMS FOR RAPID DETECTION OF MICROORGANISMS USING FREE ANTIBODIES

RELATED APPLICATIONS

The present application claims priority to U.S. Provisional Patent Application No. 61/940,968, filed Feb. 18, 2014. The disclosure is hereby incorporated by reference in its entirety herein.

FIELD OF THE INVENTION

This invention relates to methods and systems for the detection of microorganisms.

BACKGROUND

There is a strong interest in improving speed and sensitivity for detection of bacteria, viruses, and other microorganisms in both biological and food-based samples. Microbial pathogens can cause substantial morbidity among humans and domestic animals, as well as immense economic loss. Also, detection of microorganisms is a high priority for the Food and Drug Administration (FDA) and Centers for Disease Control (CDC) given outbreaks of life-threatening or fatal illness caused by ingestion of food contaminated with certain microorganisms, e.g., *Escherichia coli* or *Salmonella* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, these methods have drawbacks. For example, techniques involving direct immunoassays or gene probes generally require an enrichment step in order to obtain adequate sensitivity. Polymerase chain reaction (PCR) tests also include an amplification step and therefore are capable of both very high sensitivity and selectivity, however, the sample size that can be economically subjected to PCR testing is limited. With dilute bacterial suspensions, most small subsamples will be free of cells and therefore enrichment steps are still required.

The time required for traditional biological enrichment is dictated by the growth rate of the target bacterial population of the sample, by the effect of the sample matrix, and by the required sensitivity. For instance, a magnetic-capture PCR system for verotoxigenic *E. coli* can require about 5, 7 and 10 hours of culturing for enrichment to detect 1000, 100, and 1 colony forming unit per milliliter (CFU/mL), respectively, in a model system, and 15 hours of culturing for enrichment to detect 1 CFU per gram (g) in ground beef. In practice, most high sensitivity methods employ an overnight incubation and take about 24 hours overall. Due to the time required for cultivation, these methods can take up to three days, depending upon the organism to be identified and the source of the sample. This lag time is generally unsuitable as the contaminated food, water (or other product) may have already made its way into livestock or humans. In addition, increases in antibiotic-resistant bacteria and biodefense considerations make rapid identification of bacterial pathogens in water, food and clinical samples critical priorities worldwide.

Therefore, there is a need for more rapid, simple and sensitive detection and identification of microorganisms, such as bacteria, viruses, and other potentially pathogenic microorganisms.

SUMMARY OF THE INVENTION

In one aspect, the present invention utilizes binding agents for rapid detection of a microorganism in a sample. A variety of microorganisms can be detected using the methods described herein. The invention may be embodied in a variety of ways.

For example, in one embodiment, the present invention comprises a method for detecting a microorganism of interest in a sample, comprising the steps of: capturing the microorganism from the sample on a solid support, incubating the sample with a detection antibody specific for the microorganism of interest, wherein the detection binding agent comprises an indicator moiety; washing the captured microorganism sample to remove unbound antibody, and detecting the indicator moiety, wherein positive detection of the indicator moiety indicates that the microorganism is present in the sample.

In another embodiment, the present invention comprises a system for detecting a microorganism of interest in a sample, comprising a component for incubating the sample with a detection antibody specific for the microorganism of interest, wherein the detection antibody comprises an indicator moiety, a component for capturing the microorganism of interest from the sample on a solid support, a component for washing the captured microorganism sample to remove unbound antibody, and a component for detecting the indicator moiety.

Also, in some embodiments, components of the system of the invention may be presented as a kit. In some embodiments, a kit for rapid detection of a microorganism of interest in a sample comprises free antibodies specific for the microorganism of interest.

In some embodiments, the invention comprises computer readable media designed for use with the methods or systems as described further herein.

Other aspects of the methods and systems of the invention are described in more detail herein.

Thus, some embodiments of the present invention rely on antibody-based methods for amplifying a detectable signal to indicate the presence of specific microorganisms. The principles applied herein can be applied to the detection of bacteria or other microorganisms. Because of the large number of binding sites on the surface of a microorganism, the antibodies or other binding agents may be more readily detectable than the microorganisms themselves. In this way, embodiments of the present invention can achieve tremendous amplification of signal from a single cell.

BRIEF DESCRIPTION OF THE FIGURES

The present invention may be better understood by referring to the following non-limiting figures.

DETAILED DESCRIPTION OF THE INVENTION

Figure 1:
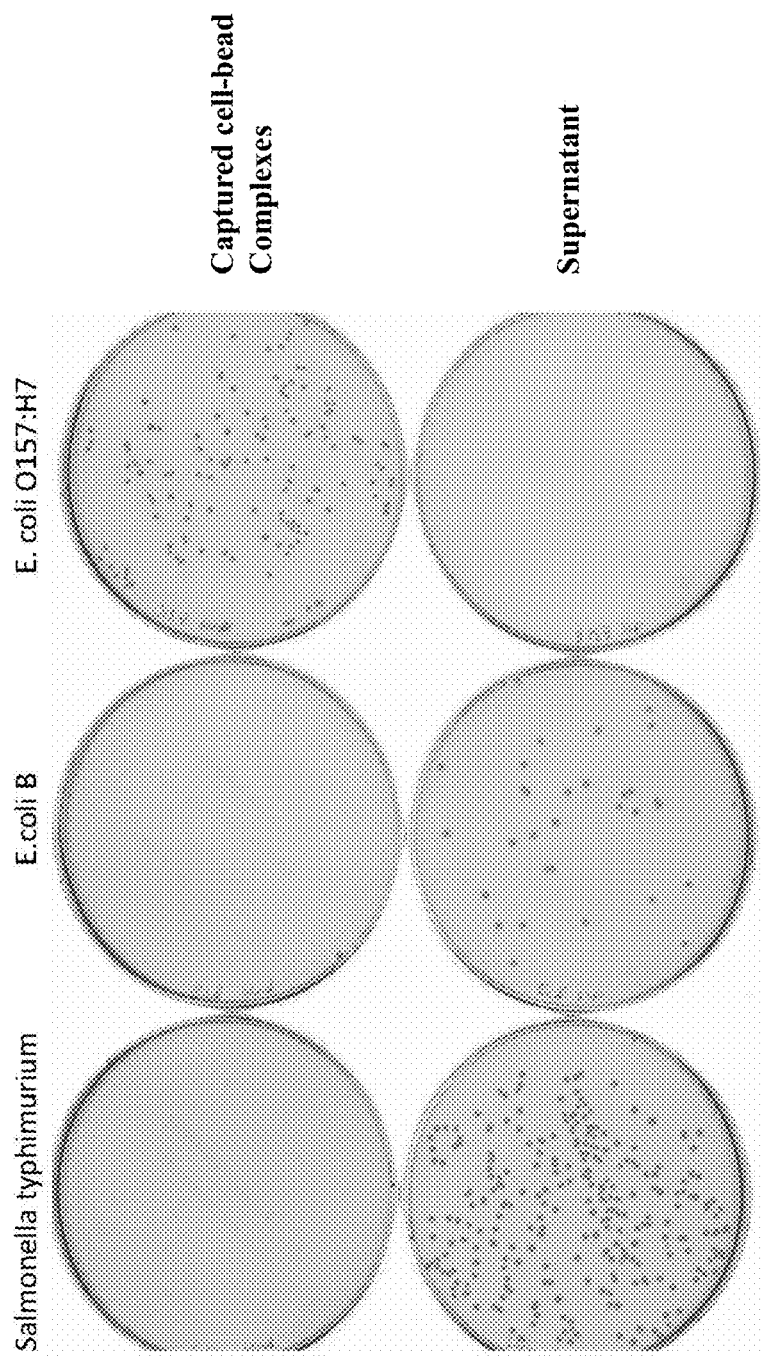
FIG. 1 demonstrates the specificity achieved with binding agents of the invention and shows the specific and quantitative capture of *E. coli* O157:H7 cells from a sample using affinity-purified and reverse-purified surface-specific antibodies, according to an embodiment of the invention.

The present invention utilizes the high specificity of binding agents that can bind to particular microorganisms as a means to detect the presence of and/or quantify the specific microorganism in a sample.

Disclosed herein is the discovery that surprising sensitivity for detection of a microorganism of interest in test samples (e.g., biological, food, water, and clinical samples) can be achieved in a shorter time frame than was previously thought possible using signal amplification in assays performed without any culturing for enrichment, or in some embodiments with minimal incubation times during which microorganisms could potentially multiply.

Embodiments of the methods and systems of the invention can be applied to detection and quantification of a variety of microorganisms (e.g., bacteria, fungi, yeast) in a variety of circumstances, including but not limited to, detection of pathogens from food, water, clinical and commercial samples. Antibody-based detection embodiments are relatively fast and require only inexpensive, simple reagents and equipment. The antibody-based embodiments disclosed herein may be adapted to any bacterium or other microorganism of interest (e.g., pathogenic microorganism) for which surface-specific antibodies are available which do not cross-react with other microorganisms. The methods of the present invention provide high detection sensitivity and specificity rapidly and without the need for traditional biological enrichment (e.g., culture). Thus, a variety of microorganisms may be detected using the methods of the invention.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate onto which biomolecules may be bound. For example, a solid support may be an assay well (i.e., such as a microtiter plate), or the solid support may be a location on a filter, an array, or a mobile support, such as a bead.

The term "antibody" includes monoclonal antibodies, polyclonal antibodies, synthetic antibodies and chimeric antibodies, e.g., generated by combinatorial mutagenesis and phage display. The term "antibody" also includes mimetics or peptidomimetics of antibodies. Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like. "Surface-specific antibodies" as used herein bind to molecules exposed on the outer surface of a specific microorganism.

The term "binding agent" refers to a molecule that can specifically and selectively bind to a second (i.e., different) molecule of interest. The interaction may be non-covalent, for example, as a result of hydrogen-bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator moiety" refers to a molecule that can be measured in a quantitative assay. For example, an indicator moiety may comprise an enzyme that is able to convert a substrate to a product that can be measured (e.g., a visible product). For example, an indicator moiety may be an enzyme that catalyzes a reaction to generate bioluminescence (e.g., luciferase). Or, an indicator moiety may be a radioisotope that can be quantified. Or, an indicator moiety may be a fluorophore. Or, other indicator molecules may be used.

As used herein, the term "free antibodies" refers to antibodies which are in solution and may move freely through a liquid, i.e., they are not initially bound to a solid support or otherwise constrained.

As used herein, "affinity-purified" or "affinity-purification" refers to a series of steps used to prepare and treat antibodies such that they exhibit optimal specificity and sensitivity, including minimal cross-reactivity with undesired epitopes. For example, removal of undesired lipids and proteins from antiserum may first be achieved by salt precipitation steps. Further positive selection by the active selection of the antibody (also called "affinity-purification") and/or negative selection by the active removal of antibodies other than target-specific antibodies (also called "reverse-purification") may be achieved by passing the remaining antibodies over agarose columns designed to retain antibodies with particular non-target epitope affinities. In some examples, where the starting antiserum is polyclonal, the purified antibodies that remain after these selection steps are able to recognize many different epitopes on the surface of the microorganism of interest, but they do not recognize the surface epitopes of other microorganisms.

As used herein "non-specific" in reference to an antibody, means that the interaction between the antibody and a target is not due to a specific binding of an epitope, but instead is the result of other types of adsorption and/or interaction that may occur between and antibody and a target (e.g., protein, biomolecule, solid surface, etc.).

Methods for Detecting Microorganisms using Free Binding Agents

In some embodiments, the invention comprises a method for rapid detection of a microorganism of interest in a sample, comprising capturing the microorganism from the sample on a solid support, incubating the microorganism sample with a detection antibody specific for the microorganism of interest, wherein the detection antibody comprises an indicator moiety, and detecting the indicator moiety, wherein positive detection of the indicator moiety indicates that the microorganism is present in the sample.

In some embodiments, the method further comprises washing the captured microorganism sample to remove unbound antibody. In either of the above embodiments, the detection antibody may be a free antibody specific for surface antigens of the microorganism. In some embodiments, the solid support may be a filter which captures the microorganism of interest based on size. In some embodiments, at least 60% of the detection antibody binding sites on the surface of the microorganism are bound to detection antibody following the incubating step. In some embodiments, at least 100,000 detection antibodies are bound to the surface of a single cell of the microorganism. Some embodiments of these methods further comprise a centrifugation step.

In some aspects, the methods can detect as few as 1 to 3 cells of the microorganism in the sample. In some embodiments, the total time required for detection is less than 2 hours. Some methods further comprise a high-salt washing step, for example a wash comprising greater than 0.25 M NaCl and greater than 0.25% Tween20. In some embodiments the indicator moiety is an enzyme. In some embodiments, the enzyme may be horseradish peroxidase or luciferase. In some such embodiments, incubation with a reactive substrate produces a detectable signal which corresponds to the amount of enzyme present.

In some methods of the invention, the capturing step further comprises binding the microorganism with a capture antibody. In some embodiments a moiety conjugated to the capture antibody facilitates binding of the microorganism to a solid support. In some embodiments the ELISA plate is first coated with capture antibody, and then the sample is applied to the ELISA plate. In some embodiments using ELISA plates, the ELISA plate further comprises a white or colored background or a combination of white and colored background.

In some methods of the invention, the incubating step further comprises addition of an excess of non-specific, non-labeled blocking antibody derived from the same species as the detection antibody. In some method embodiments, the filter comprises a hydrophilic membrane which exhibits low protein binding capacity.

In some embodiments, the capture antibody and/or the detection antibody is affinity-purified and/or reverse-purified. In some embodiments, the microorganism comprises at least one of a bacterium, or a fungus, or a yeast, or a virus.

Thus, embodiments of the invention disclosed and described herein utilize the discovery that a single microorganism is capable of binding a surprisingly large number of specific recognition agents, such as antibodies. For example, antibodies specific to surface antigens associated with a particular microorganism are appropriate binding agents. Antibody fragments or other molecules may also be suitable binding agents. Surface-specific antibodies or antibody fragments may be generated against antigens found on the surface of a specific microorganism of interest. As such, antibodies or antibody fragments can specifically identify a microorganism for capture or detection purposes or both.

Embodiments of the methods and systems of the invention can be applied to detection and quantification of a variety of microorganisms (e.g., bacteria, fungi, yeast) in a variety of circumstances, including but not limited to detection of pathogens from food, water, clinical and commercial samples. For example, the methods may be applied to the detection of bacteria, yeast, fungi, or other microorganisms. Bacterial cells detectable by the present invention include, but are not limited to, all species of *Salmonella*, all species of *Escherichia coli*, including, but not limited to *E. coli* O157:H7, all species of *Listeria*, including, but not limited to *L. monocytogenes*, and all species of *Campylobacter*. Bacterial cells detectable by the present invention include, but are not limited to, bacterial cells that are pathogens of medical or veterinary significance. Such pathogens include, but are not limited to, *Bacillus* spp., *Bordetella pertussis, Camplyobacter jejuni, Chlamydia pneumoniae, Clostridium perfringens, Enterobacter* spp., *Klebsiella pneumoniae, Mycoplasma pneumoniae, Salmonella typhi, Shigella sonnei, Staphylococcus aureus*, and *Streptococcus* spp.

Thus in some embodiments, the microorganism of interest comprises at least one of a bacterium, or a fungus, or a yeast, or a virus.

The embodiments disclosed herein may be adapted to any microorganism of interest for which surface-specific biomolecules are available which bind to specific binding agents and do not cross-react with other microorganisms. The methods of the present invention provide high detection sensitivity and specificity rapidly and without the need for traditional biological enrichment (e.g., culture). Thus, a variety of microorganisms may be detected using the methods of the invention.

For example, disclosed is the finding that a single *E. coli* cell may bind more than $2 \times 10^5$ antibodies. This principle allows amplification of signal from one or a few cells based on specific recognition of microorganism surface antigens (e.g., by a plurality of antibodies). Antibodies may be bound to a large number of the available binding sites on the surface of a microorganism. In some embodiments, the microorganism is detectable at very low levels as a result of this amplification (e.g., a single microorganism may be detected).

In some embodiments, detection is achieved through an indicator moiety associated with the binding agent specific for the microorganism of interest. For example, an indicator moiety may be associated with antibodies or antibody fragments. Also, in some embodiments, detection is achieved without the use of a second binding agent to purify the complex of the antibody bound to the microorganism of interest.

Thus, in certain embodiments, the present invention comprises a method for rapid detection of a microorganism of interest in a sample, comprising: capturing the microorganism from the sample on a solid support; incubating the microorganism sample with a detection binding agent specific for the microorganism of interest, wherein the detection binding agent comprises an indicator moiety; and detecting the indicator moiety, wherein positive detection of the indicator moiety indicates that the microorganism is present in the sample. In an embodiment, the method may comprise the step of washing the captured microorganism sample to remove unbound detection binding agent.

Antibodies for Targeting the Microorganism of Interest

In an embodiment, the detection binding agent is an antibody.

For example, in certain embodiments, the present invention comprises a method for rapid detection of a microorganism of interest in a sample, comprising: capturing the microorganism from the sample on a solid support; incubating the microorganism sample with a detection antibody specific for the microorganism of interest, wherein the detection antibody comprises an indicator moiety; and detecting the indicator moiety, wherein positive detection of the indicator moiety indicates that the microorganism is present in the sample. In an embodiment, the solid support is a filter plate. In another embodiment, the solid support is an ELISA plate. In some embodiments, the method may comprise the step of washing the captured microorganism sample to remove unbound antibody.

In an embodiment, the detection antibody is a free antibody specific for surface antigens of the microorganism. Thus, in certain embodiments, the present invention utilizes the high specificity of binding agents that can recognize and/or bind to a particular microorganism of interest as a means to amplify a signal and thereby detect low levels of a microorganism (e.g., a single microorganism) present in a sample.

In some embodiments, saturation of a high percentage of available surface antigens enables detection of microorganisms with heightened sensitivity and specificity. In alternate embodiments, at least 20%, 30%, 40%, 50%, 55%, 60%, 65%, 70%, 75%, 80%, 85%, 90%, or greater than 95% of the antibody binding sites on the surface of the microorganism are bound to antibody following the incubating step. In some embodiments, at least 10,000; 20,000; 30,000; 40,000; 50,000; 60,000; 70,000; 80,000; 90,000; 100,000; 110,000; 120,000; 130,000; 140,000; 150,000; 160,000; 170,000; 180,000; 190,000; or 200,000 antibodies or antibody fragments are bound to the surface of a single microorganism cell.

Given the large number of binding sites available on the surface of a single microorganism, exposure of microorganisms in a sample to an excess of specific antibody molecules may allow greater saturation of potential binding sites. For example, in some embodiments a single sample may be exposed to greater than $1\times10^{10}$ antibody molecules. In some embodiments, a single sample may be exposed to greater than $4\times10^{10}$ antibody molecules. In some circumstances, any number in the range of 1 ng ($4\times10^9$) to 250 ng ($1\times10^{12}$) antibody molecules per sample may also be appropriate.

Appropriate antibodies or antibody fragments may be conjugated to horseradish peroxidase (HRP) or another suitable indicator moiety (also called detection moiety), depending on the embodiments of the invention being employed. In certain embodiments, the antibody is affinity purified and/or reverse-purified.

Antibodies demonstrating specific recognition of surface antigens on a wide variety of bacteria or other microorganisms are available commercially from a number of sources. For example, purified surface-specific antibodies from whole serum may be obtained from Kirkegaard & Perry Laboratories, Inc. (KPL). Another commercial source for such antibodies is Abcam. In some embodiments, the antibodies are subjected to affinity-purification and/or reverse-purification (also called "positive selection" and/or "negative selection"), such that cross-reactivity to undesired antigens, such as those on the surface of other closely related microorganisms, is minimized.

Positive selection may involve covalently coupling antigens to an agarose support (e.g., done in batch or column) and then applying the antiserum. The desired antibodies from the antiserum bind the antigens, while other proteins and non-specific antibodies are washed away. The antigen-specific antibodies are then eluted from the agarose support. This product is the "affinity-purified antibody" fraction.

The affinity-purified antibody may then be further purified by "reverse purification" or "negative selection." Again, antigens are coupled to the agarose support, but instead of using target antigens, negative selection employs antigens from other targets. Undesired antibodies bind the antigens and remain on the support, while the desired antibodies pass through for collection. The final product is both affinity-purified and "reverse purified," and thus it may be highly specific for the target of interest (e.g., *E. coli* O157:H7).

Thus, in some embodiments of the invention, purified surface-specific antibodies that recognize a particular microorganism (e.g., *E. coli* O157:H7) do not recognize other similar microorganisms (e.g., *E. coli* B). Also in some embodiments, antibodies specific to, e.g., *E. coli* B or *E. coli* O157:H7 do not recognize cells of *Salmonella typhimurium* or *Staphylococcus epidermidis* or other microorganisms. This represents another surprising discovery, as many microorganisms have, e.g., surface lipopolysaccharide (Gram-negative bacteria) or lipoteichoic acid (Gram-positive bacteria) molecules that were previously believed to be highly similar, especially between closely related species. The specificity of antibodies that recognize *E. coli* O157:H7, but that do not recognize *E. coli* B and *Salmonella typhimurium* is shown in FIG. 1 discussed in more detail below.

Capturing the Microorganism

In some embodiments, the present invention comprises methods and systems that allow physical capture, collection, or isolation of bacterial cells from a sample. Such capture may be based on binding agent specificity or other features of the microorganism such as size. For example, a single bacterium, which may have a volume of about one cubic micrometer, can be isolated from a one-milliliter sample having a volume of $10^{12}$ cubic micrometers. In some embodiments, capture facilitated by a specific binding agent (e.g., capture antibodies) may be desirable to increase the concentration of the microorganism in the sample. In such embodiments the method may include the step of contacting the sample with a plurality (an excess) of free affinity-purified capture antibodies or antibody fragments.

Additionally or alternatively, a solid support can be used to capture the microorganism of interest. For example, a solid support can be used to capture the microorganism based on a size separation of the microorganism away from other components in the sample. Thus, in one embodiment, the solid support is a filter which captures the microorganism based on size. For example, filtering a sample through a bacteriological filter (e.g., 0.45 μm pore size spin filter) allows smaller substances to pass through while retaining intact bacteria. Alternatively, a plate filter may be used to capture a microorganism, or a variety of other filter devices may be used (e.g., 96-well filter plate).

Thus, some embodiments of the present invention comprise a step for collecting or capturing the microorganism on a bacteriological filter by size-fractionation. In some embodiments, size-based capture is the first step. In some embodiments, the next step employs a binding agent that specifically targets the microorganism of interest, facilitating detection. For example, a detection antibody may be incubated with the captured microorganism, in order to specifically target and identify the microorganism of interest. Other methods of physical and/or chemical isolation of the microorganisms in the sample may be used. In various embodiments, detection steps may be performed before, simultaneously with, or after such capture.

In certain embodiments, a detectable moiety present in the assay sample can contribute to background signal (i.e., a signal detected even when no cells of the microorganism are present). For example, in certain embodiments, background signal may result from a detection antibody binding to various components of the assay (e.g., plate surface, other non-target cells). Antibodies may bind specifically or non-specifically, both of which contribute background signal. However, to increase sensitivity of the assay, it may be desirable to incubate the microorganism of interest with an excess of detection antibody specific for the target microorganism. Thus, there is a balance between sensitivity and specificity.

In certain embodiments, the solid support is a material that is hydrophilic and so does not bind protein in a non-specific manner. In one embodiment, the solid support is a hydrophilic membrane that exhibits low protein binding capacity. For example, 0.45 hydrophilic-PVDF filter plates (Whatman catalog #7700-3306) that are pre-blocked with 1% BSA/PBST, are appropriate low protein binding filter plates. Alternatives are available from Pall (0.45 μm Supor (polyethersulfone) membrane plate with low protein binding (AcroPrep #6008029) and Millipore (Durapore Multiscreen Plates, low protein binding, hydrophilic PVDF).

Additionally or alternatively, to reduce any non-specific binding of the detection antibody to the solid support (or other components present in the assay), the incubating step may further comprise addition of an excess of a non-labeled blocking antibody. The non-labeled blocking antibody may be an antibody that is not specific to the microorganism of interest (i.e., does not recognize a specific epitope of the microorganism of interest). The non-labeled antibody may be derived from the same species as the detection antibody. For example, if the detection antibody is derived from goat, then a vast excess of non-specific IgG also derived from goat may be added to the assay. By including a large molar excess of non-specific (non-labeled) antibody, the non-labeled antibody may reduce non-specific binding of the reporter-antibody molecule. Thus, using an antibody as a blocker can serve as a better blocker than a general protein (e.g., BSA) if the reporter is antibody-based. Using paired antibodies (i.e., detection antibody and blocking antibody) from the same species may improve the blocker's effectiveness.

In certain embodiments, the method includes one or more steps of washing, for example washing the captured microorganism of interest with a high-salt formulation to remove any extra particles that may contribute to high background signal. Also, a high-salt washing step may be used after the detection antibody incubation to remove any excess detection antibody that may be present. For example, in an embodiment, the method may comprise washing the complex of the microorganism of interest that has been incubated with antibody in a high-salt wash. The high-salt wash may comprise, for example a solution of greater than 0.25 M NaCl, and greater than 0.25% Tween 20, or either the NaCl component or the Tween20 component alone. Other high-salt options include solutions with NaCl up to 350 mM, Triton X-100 detergent at 0.05% (or lower/higher), CHAPS detergent at 0.05% (or lower/higher), a Tris-based buffer (TBS) instead of phosphate-buffer (PBS), or others.

The method may comprise capturing the microorganism on a solid support and then adding the binding agent to form a complex of microorganism and binding agent on the solid support. Or, the method may comprise forming a complex of microorganism and binding agent and capturing the microorganism as the complex on a solid support.

Thus, in some embodiments the invention comprises a method for rapid detection of a microorganism of interest in a sample, comprising the steps of: capturing the microorganism from the sample on a solid support; incubating the sample with a detection antibody specific for the microorganism of interest, wherein the detection antibody comprises an indicator moiety; washing the captured microorganism sample to remove unbound antibody; and detecting the indicator moiety, wherein positive detection of the indicator moiety indicates that the microorganism is present in the sample.

Alternatively, the sample may be captured on a filter after incubation with detection antibody (i.e., the first two steps above are reversed). Thus, in some embodiments, the target microorganism may be detected by incubating the sample being tested with a detection antibody, capturing the microorganism on a bacteriological filter, washing excess antibody away, and measuring the amount of indicator moiety present by incubating with an appropriate reactive substrate on the sample captured by the filter.

Use of Binding Agents to Capture Microorganisms of Interest from a Sample

In certain embodiments, binding agents with high specificity for a microorganism of interest may be employed to facilitate capture and isolation of low levels of a microorganism (e.g., a single microorganism) present in a sample. Thus, in certain embodiments, the capturing step comprises binding the microorganism of interest to a capture antibody.

For example, in some embodiments a capturing step of the invention may utilize capture antibodies specific for the microorganism to facilitate isolation of the microorganism from other components in the sample. In some embodiments, the capture antibody and detection antibody may be the same antibody except that they are conjugated to different chemical moieties.

For example, a capture antibody may be biotinylated to facilitate binding to streptavidin bound to a solid support, while a detection antibody conjugated to HRP may be employed to facilitate emission of a visual signal upon incubation with appropriate substrate. However, in such an embodiment, binding sites occupied by capture antibody may effectively reduce the binding sites available for detection antibody. Still such an embodiment may be used where the sample amount is not limiting and simplicity of the assay format is preferred (e.g., field tests for microorganisms).

For example, FIG. 1 demonstrates the specificity of *E. coli* O157:H7 capture facilitated by capture antibodies, where other types of microorganisms are also present in the test sample, namely *E. coli* B and *Salmonella typhimurium*. In this colony forming unit (CFU) experiment, magnetic beads coated with streptavidin were used to isolate *E. coli* O157:H7 preincubated with free biotinylated polyclonal antibodies (KPL) produced against intact *E. coli* O157:H7 and affinity-purified to minimize cross-reactivity with other microbial species. After capture on magnetic beads, a portion of the sample of cell-bead complexes was spread on Luria Bertani (LB) plates and incubated at 37° C. overnight to allow colonies to grow (CFU assay). It was found that the *E. coli* O157:H7 cells were only present in the cell-bead complex fraction when specific *E. coli* O157:H7 antibodies were used, and no *E. coli* O157:H7 bacteria were recovered in the supernatant fraction. *E. coli* B and *S. typhimurium* cells were found only in the supernatant fraction when *E. coli* O157:H7-specific antibodies were used. In the absence of antibody, all three types of bacteria were found in the supernatant fraction.

Alternatively, in some embodiments, a bead coated with another chemical moiety that binds to the microorganism-antibody complex may be used. For example, a bead coated with a secondary antibody that recognizes or binds the anti-bacterium antibody may be used. At this point, the bacteria bound to the beads may be isolated from the sample (e.g., by aspiration, decanting, magnetic force, or other appropriate isolation methods) and detected by a variety of techniques. In some embodiments, the efficiency of capture may be quantified by plating the bacteria bound to the beads and the unbound supernatant fraction in a CFU assay, similar to the experiment demonstrated in FIG. 1. In other embodiments, the signal generated by reaction with substrate (i.e., substrate reagent) for detection of indicator moiety is measured in a portion of the captured sample for comparison with the plated portion.

Thus, in some embodiments, the method may comprise first incubating the sample with biotinylated capture antibody; next contacting the sample with a plurality of magnetic streptavidin-coated beads to bind the bacterium-antibody complex; and finally sequestering the bead-antibody-bacterium complex with a magnet to isolate the bacteria. Or, other methods of purifying the biotin-antibody: bacterium complex may be used. With such embodiments, a bacterium in a one-milliliter sample can be concentrated to about one microliter (~1000-fold), facilitating further detection and/or quantification by methods described herein.

Capturing Microorganisms Using an ELISA Assay

In other embodiments, a capture binding agent may first be immobilized to the surface of a microtiter plate before a sample to be tested for the target microorganism is added. In an embodiment, the capture antibody is bound to a solid support. In an embodiment, the solid support is an ELISA plate. In an embodiment, a moiety conjugated to the capture antibody facilitates binding of the microorganism to a solid support. For example, in certain embodiments a plate is first coated with capture antibody, and then the sample is applied to the plate. The plate may be white or in alternate embodiments, the plate may have a colored background or a combination of white and colored background.

Thus, in an embodiment the present invention comprises a method for rapid detection of a microorganism of interest in a sample, comprising: capturing the microorganism from the sample on a solid support comprising a binding agent bound to the solid support and that specifically binds the microorganism of interest; incubating the microorganism sample with a detection binding agent specific for the microorganism of interest, wherein the detection binding agent comprises an indicator moiety; and detecting the indicator moiety, wherein positive detection of the indicator moiety indicates that the microorganism is present in the sample.

In an embodiment, the binding agent used for capture and/or the binding agent used for detection is an antibody. Thus, in certain embodiments, the present invention comprises a method for rapid detection of a microorganism of interest in a sample, comprising: capturing the microorganism from the sample on a solid support comprising antibody bound to the solid support, but that specifically binds the microorganism of interest; incubating the microorganism sample with a detection antibody specific for the microorganism of interest, wherein the detection antibody comprises an indicator moiety; and detecting the indicator moiety, wherein positive detection of the indicator moiety indicates that the microorganism is present in the sample.

The capture binding agent may be a polyclonal antibody or it may be a monoclonal antibody. A monoclonal capture antibody may also greatly reduce background signal (as compared to a polyclonal), allowing for better sensitivity. This may be explained by the similarity of surface proteins among a large variety of bacterial cells that are found in a vegetable wash, such that a polyclonal antibody could capture non-target cells (which in some test samples could greatly outnumber target cells).

In some embodiments, the sample is centrifuged to increase the proximity of the microorganism to the capture antibody, facilitating the capture step. The sample wells may be washed after incubation for a length of time sufficient for antibody binding, to allow for efficient capture of the target microorganism before removal of other components in the sample. Thus, some embodiments allow capture and immobilization of the target microorganism on the surface of a microtiter plate using capture antibodies.

In some aspects, an atypically large number of capture antibody molecules may increase the capture efficiency for the particular microorganism of interest. For example, experiments with three times the recommended amount of monoclonal antibody used to coat ELISA plates yielded better results than a more typical amount. More specifically, 300 ng, or $1.2 \times 10^{12}$ monoclonal antibodies, in 100 µL volume, instead of typical 100 ng, or $4 \times 10^{11}$ antibodies, in 100 µL volume, yielded better results for coating one well of a 96-well ELISA plate and capturing $E.\ coli$ O157:H7. In other respects the ELISA plate is coated with antibody according to standard procedures.

Thus, in some embodiments, an affinity-purified antibody may be used to facilitate capture of the microorganism of interest on a solid support. In an embodiment, the solid support for capture may be an assay well (e.g., a microtiter plate) or a filter. Or, the capture solid support may be a location on an array, or a mobile support, such as a bead. In an embodiment, the binding agent is immobilized on a solid support (e.g., filters or beads or surface of microtiter plate) or is free and subsequently immobilized on a solid support. The immobilized microorganism may then be removed from the sample (e.g., by aspiration, decanting, magnetic force, or other appropriate isolation methods) and detected by a variety of techniques.

Detecting the Microorganisms

In some aspects, the present invention provides methods for detection of microorganisms through an indicator moiety. In some embodiments, the indicator moiety may be conjugated to a microorganism-specific antibody ("detection antibody"). In some embodiments, the indicator moiety may react with a substrate to emit a detectable signal. In some embodiments, the detection sensitivity can reveal the presence of as few as 100, 50, 40, 30, 20, 10, 5, 4, 3, or 2 cells of the microorganism of interest. In some embodiments, even a single cell of the microorganism of interest may yield a signal detectably higher than background signal.

In some embodiments, methods of the invention require a total of less than 3.5 hours, less than 3 hours, less than 2.5 hours, less than 2 hours, less than 1.5 hours, or less than 1 hour for detection of a microorganism of interest. In some embodiments, these rapid methods can detect as few as 100, 75, 50, 20, 10, 9, 8, 7, 6, 5, 4, 3, or 2 cells of the microorganism of interest. In some embodiments, even a single cell of the microorganism is detectable.

Aspects of some embodiments of methods for detecting a microorganism of interest may benefit from use of a polyclonal antibody as the detection antibody. Use of a polyclonal antibody may facilitate binding to more sites on the surface of a microbial cell and may increase the sensitivity of the assay.

In some embodiments the detection antibody is conjugated to an enzyme which may serve as the indicator moiety. In certain embodiments, the method includes incubation with a reactive substrate so as to produce a detectable signal which corresponds to the amount of enzyme present. Many indicator moieties are commercially available, as are detection antibodies conjugated to such indicator moieties. For example, horseradish peroxidase (HRP) or luciferase or another appropriate enzyme (e.g., alkaline phosphatase) may be conjugated to an antibody or antibody fragment. Alternatively, other enzyme-substrate combinations may also be used as the indicator combination.

Generally, such enzymes react with appropriate substrates to catalyze multi-step reactions which are accompanied by emission of light, conversion of a substrate to a colored compound or conversion of a substrate to a compound that may be detected by other means. The signal (e.g., light emission, color) may be analyzed quantitatively in an appropriate machine (e.g., luminometer, spectrophotometer). For example, luciferase may serve as the indicator moiety and luciferin as the substrate, or other luciferase substrates may be used. Alternatively, the detection antibody may be labeled with a fluorescent moiety (e.g., fluorophores, QDOTS®). Any such detection antibody may be used with various embodiments of the invention.

A luminometer may be used to detect the color or other light emissions in some embodiments described herein. However, other devices or machines may also be used. For example, a spectrophotometer, a CCD camera, or CMOS camera may be used to detect color changes and other light emissions. Chemiluminescent assays generally demonstrate higher sensitivity, while colorimetric approaches generally demonstrate lower sensitivity. Colorimetric equipment may be more widely available and less expensive, however.

In many embodiments, multi-well plates are used to conduct the assays. The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

A variety of indicator moieties may be used. Some embodiments of the present invention utilize detection antibody conjugated to a reporter or indicator, such as horseradish peroxidase (HRP). In some embodiments, HRP-antibody-cell complexes may be reacted with an appropriate substrate, such as 3,3',5,5'-Tetramethylbenzidine (TMB), to generate a detectable indicator signal. Alternatively, the substrate may be SIRIUS®-HRP (WesternBright), or other appropriate substrates may be used. In embodiments where TMB substrate is used, the reaction of TMB with HRP generates a colorimetric signal which turns the reaction from clear to blue. The TMB reaction signal may be detected in a standard spectrophotometer at a wavelength of 650 nm. If SIRIUS® substrate is used, the reaction with HRP results in a chemiluminescent signal which may be measured in a luminometer or other device or machine. In some embodiments, SIRIUS® substrate may demonstrate higher sensitivity than TMB substrate.

For example, in some embodiments, the test sample may be incubated with free detection antibodies (e.g., specific for surface antigens of $E.\ coli$ O157:H7) coupled to HRP or another indicator moiety in solution, and the microorganism may be captured, for example, by filtering the sample through a bacteriological filter (e.g., 0.45 μm pore size spin filter) or plate filters. In an embodiment, the microorganism captured on the filter may be washed one or more times to remove excess unbound antibody. In an embodiment, the reactive substrate (e.g., TMB or SIRIUS®) may be incubated with the portion of the sample that remains bound to the filter. In an embodiment, the TMB, SIRIUS®, or other reactive substrate may then be centrifuged or drawn by vacuum through the filter and collected for detection of the indicator moiety (e.g., at 650 nm in a spectrophotometer for TMB or in a luminometer for SIRIUS® detection).

Or, as discussed above, the sample may be applied directly to the filter for capture (e.g., by centrifuge or vacuum) before incubation with a detection antibody. A detection antibody (e.g., HRP-antibody) may then be loaded onto the filter, incubated for a short time, and the excess unbound antibody may be centrifuged or drawn by vacuum through the filter. The filter-bound sample may then be washed, and a reactive substrate, such as SIRIUS®, may be loaded onto the filter and the reaction emissions measured. Thus, in some embodiments, the indicator-substrate reaction may be detected directly in the filter well.

Thus, performing the steps of the method can generate complexes comprised of the capture solid support: microorganism (cell): detection antibody: indicator moiety: substrate. Such embodiments provide for rapid analysis. In some such embodiments, no capture antibody is necessary, and no additional steps are required to physically trap the microorganism.

Alternatively, a target microorganism may be isolated and detected by simultaneously incubating the sample being tested with a capture antibody and a detection antibody, both of which may be specific to the microorganism. Or the sample may be reacted with antibodies sequentially. The microorganism may then be specifically isolated using attributes of the capture antibody. In some embodiments, the capture antibody is biotinylated such that it facilitates subsequent binding to magnetic streptavidin beads. Or the capture antibody may be conjugated to another protein or other molecule (i.e., binding agent) which facilitates linking the capture antibody to beads or another solid support. Such embodiments may provide increased sensitivity where initial sample size is large and/or very dilute.

Thus, in some embodiments, performing the steps of the method generates a variety of complexes comprised of the capture solid support: binding agent: capture antibody: surface antigen: microorganism of interest: surface antigen: detection antibody: indicator moiety: substrate or any of a variety of similar configurations.

In some embodiments, multiple microorganisms may be detected simultaneously. If more than one microorganism is to be detected, each type of detection antibody may be conjugated to a different indicator moiety. For example, detection antibody specific for $E.\ coli$ O157:H7 may be conjugated to HRP, while detection antibody specific to $S.\ aureus$ may be conjugated to alkaline phosphatase (AP). Following reaction with appropriate substrates (e.g., TMB substrate for HRP and nitroblue tetrazolium (NBT) substrate for AP), the samples may be read in the spectrophotometer at the appropriate wavelength for each microorganism to be detected (e.g., 650 nm for TMB and 405 nm for NBT). Alternatively, the sample may be divided into separate aliquots and analyzed according to various embodiments for presence of each microorganism of interest.

Figure 2:
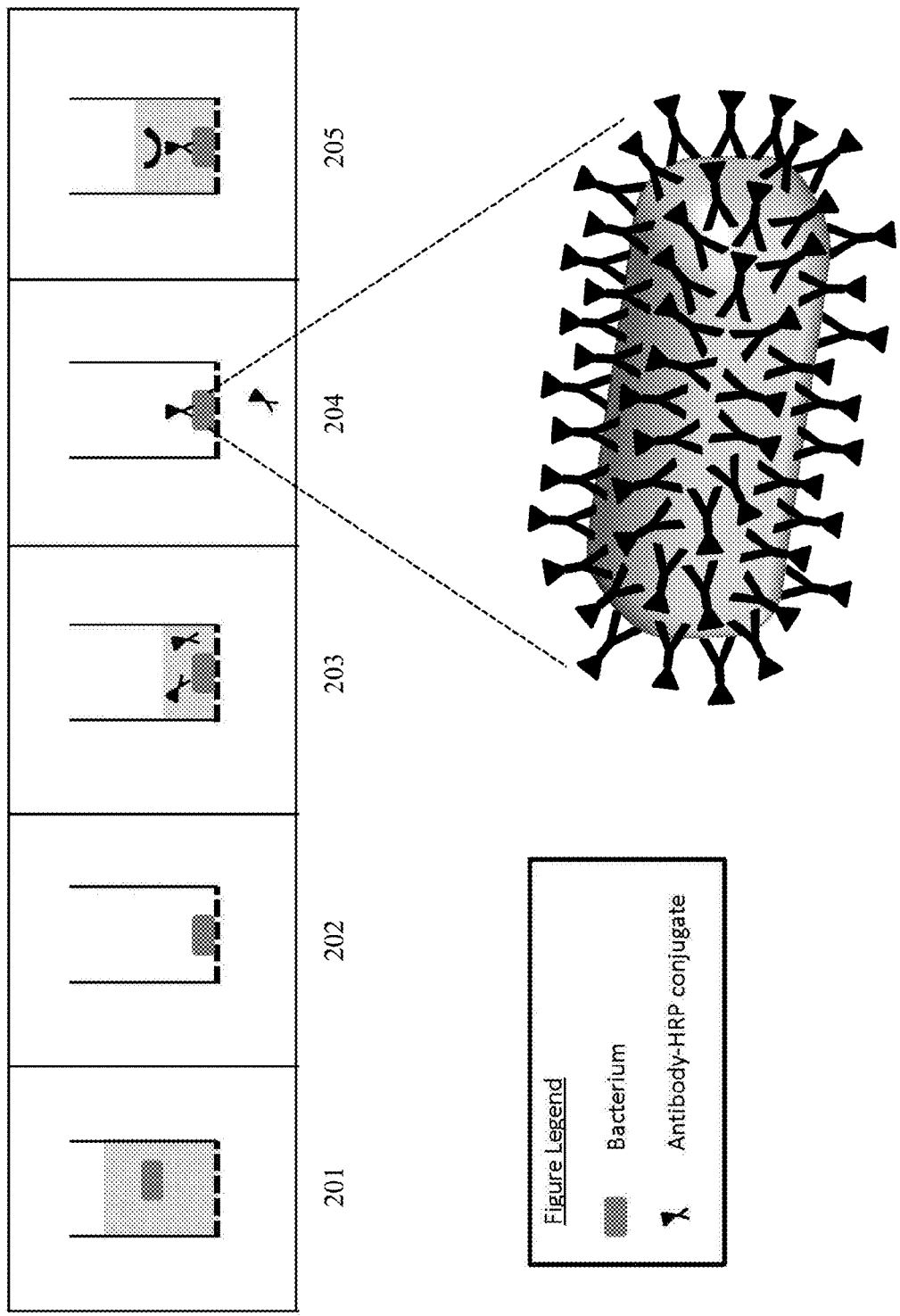
FIG. 2 illustrates a method for detection of a specific microorganism that has been captured on a solid support using a plurality of free antibodies (conjugated to HRP) to bind to a single microorganism, according to some embodiments of the invention.

FIG. 2 is a schematic showing the capture and detection of a microorganism according to one embodiment of the invention, using size-fractionation for capture on filter plates. In this embodiment, a liquid sample comprising one bacterium (as shown in the figure) or a plurality of bacteria is deposited in a well of a filter plate in step 201. The solution is removed from the well through the filter in step 202 (e.g., by vacuum or centrifugation). Next, a solution containing a plurality of free antibodies specific to a surface antigen or surface antigens (i.e. for polyclonal antibodies) on the bacteria is added to the well and incubated for a period of time (e.g., ~1 hour) sufficient to allow antibodies to bind the surface of the bacteria (step 203). The antibody may be conjugated to an indicator moiety (e.g., HRP or luciferase). Following incubation, the solution and any excess unbound antibody may be removed from the well through the filter in step 204 (e.g., by vacuum or centrifugation). Optionally, several wash steps may also be performed. Finally, detection of the indicator moiety is performed in step 205 by addition of substrate which reacts with enzyme (represented by 'U'-shaped arrow in 205). The filter plate may be placed directly in a luminometer (or other appropriate machine), the indicator substrate of choice is injected into the well (e.g., SIRIUS® or luciferase substrate reagent), and the indicator reaction signal is detected immediately after injection (and/or at other time intervals as appropriate).

The schematic diagram of FIG. 2 shows only few antibodies bound to the bacterium for simplicity, but the inset illustrates the concept that the bacterium is actually covered with tens or hundreds of thousands of antibodies (e.g. $>2\times10^5$ for $E.\ coli$ O157:H7). As about 50 antibodies are shown bound in FIG. 2 (insert), each of these antibodies depicted represents ~4,000 antibodies bound. For example, experiments comparing known amounts of HRP activity to HRP activity associated with antibodies bound to known numbers of bacteria captured in wells of a filter plate demonstrate, surprisingly, that approximately $2\text{-}5\times10^5$ HRP-Antibodies bind each *E. coli* O157:H7 cell. Thus some embodiments of the invention require a plurality of antibodies or a vast excess, sufficient to bind to a large number of binding sites available on the surface of the target microorganism. In some embodiments, a large percentage of available binding sites on a bacterium are bound to detection antibodies. In alternate embodiments, at least 20%, 25%, 30%, 35%, 40%, 45%, 50%, 55%, 60%, 65%, 70%, 75%, 80%, 85%, 90%, or 95% of the antibody binding sites on the surface of the microorganism are bound to antibody following the incubation step. For example, in alternate embodiments, at least 10,000; 20,000; 30,000; 40,000; 50,000; 60,000; 70,000; 80,000; 90,000; 100,000; 110,000; 120,000; 130,000; 140,000; 150,000; 160,000; 170,000; 180,000; 190,000; or 200,000 antibodies are bound to the surface of a single microorganism.

Thus, in some embodiments, and as illustrated in FIG. 2, the antibody is free in solution and capture of the microorganism is based on size (e.g., on filter plates). Subsequent detection of indicator moiety is performed directly on the filter plates.

In other embodiments, a detection antibody may be added to the sample (i.e., in excess as described above) in solution before capture, rather than added directly to a filter holding the captured microorganism sample. Such embodiments also utilize size-based capture in combination with specific detection antibodies. In one embodiment, the sample to be tested may first be mixed and incubated with surface-specific antibodies conjugated to HRP for approximately 1 hour. Next, the sample may be applied to a solid support, such as a bacteriological filter, by centrifugation, vacuum, or other means. The HRP substrate (TMB, SIRIUS, or other appropriate substrate) may be deposited directly in the well onto the microorganism captured on the filter (complexed with detection antibody) and allowed to react with the enzyme. The indicator signal from the reaction of HRP-antibody with substrate is detected in a luminometer (or spectrophotometer or other appropriate device), immediately after injection and/or at various time intervals thereafter.

Figure 3:
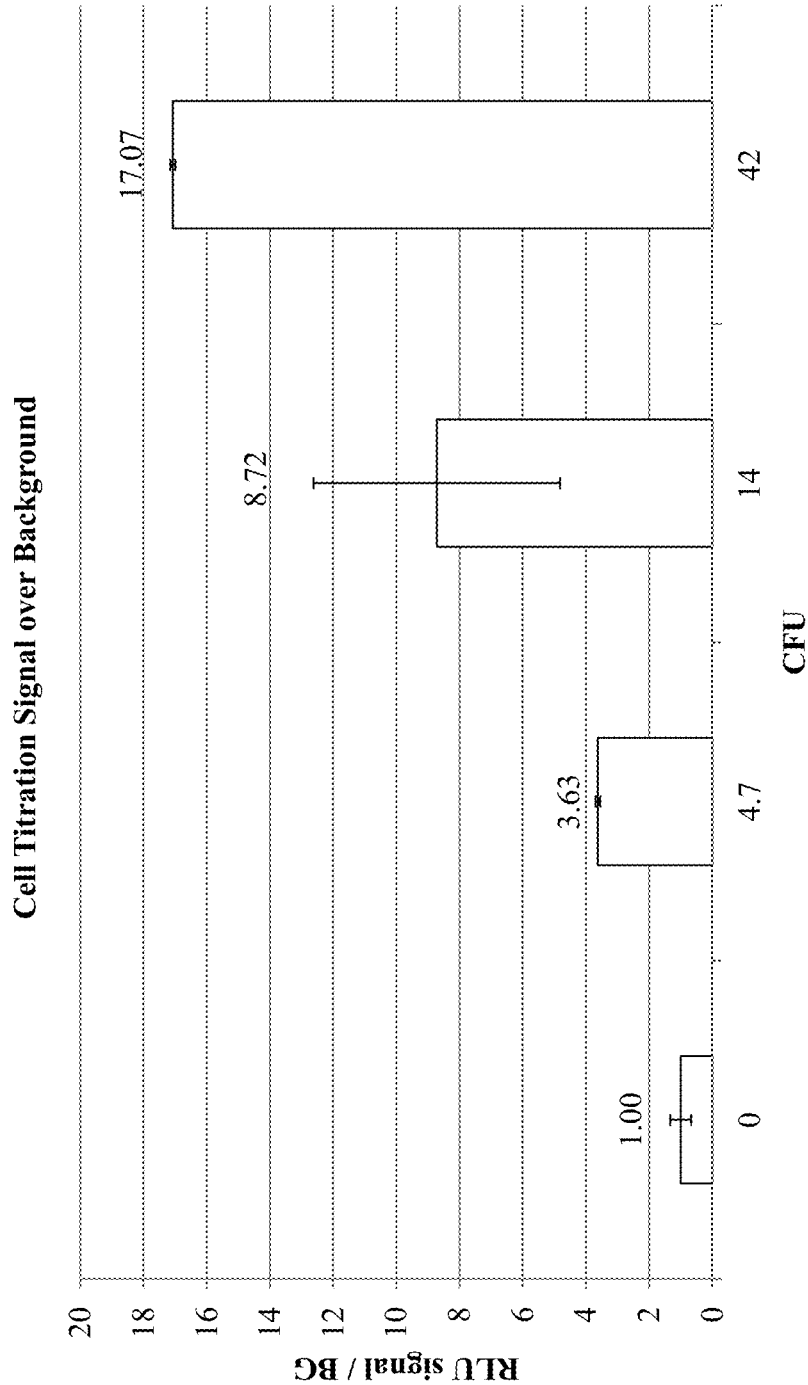
FIG. 3 demonstrates results for detection of known numbers of E. coli O157:H7 cells in a sample, using antibody specific for E. coli O157:H7 conjugated to horse radish peroxidase (HRP) according to an embodiment of the invention. In this embodiment, samples containing the E. coli O157:H7 cells were incubated with the HRP-labeled antibody specific to E. coli O157:H7 cells in a tube and then transferred to a filter plate. The number of E. coli O157:H7 cells is indicated as colony forming units (CFU) on the X-axis. The signal provided by the HRP-labeled antibody specific to E. coli O157:H7 cells is shown on the Y-axis as relative luminal units (RLU) over background (BG) signal (i.e., no cells) (RLU/BG). The substrate for the HRP was SIRIUS®. In this embodiment, the E. coli O157:H7 cells were incubated with the HRP-labeled antibody and the complex then transferred to a filter plate.

FIG. 3 demonstrates results for detection of *E. coli* O157:H7 using HRP-antibody incubated with samples in a tube and then transferred to a filter plate, according to an embodiment of the present invention. In this embodiment, samples containing known numbers of *E. coli* O157:H7 cells in a known volume of solution are incubated with anti-*E. coli* O157:H7 HRP-antibody conjugate (e.g., for ~1 hour). The entire sample may then be applied to a PVDF filter plate and washed with PBST to remove unbound antibodies. The washed plate are then placed in a luminometer where HRP chemiluminescence substrate is injected. Readings may be taken immediately after injection, as well as at appropriate intervals thereafter. The example experiment results show the number of cells (CFU) in the sample on the X-axis, and indicator signals measured over background (zero cell controls) are shown as relative luminal units (RLU) on the Y-axis. These results demonstrate that increasing indicator signal corresponds to increasing number of *E. coli* O157:H7 cells in the sample.

Figure 4:
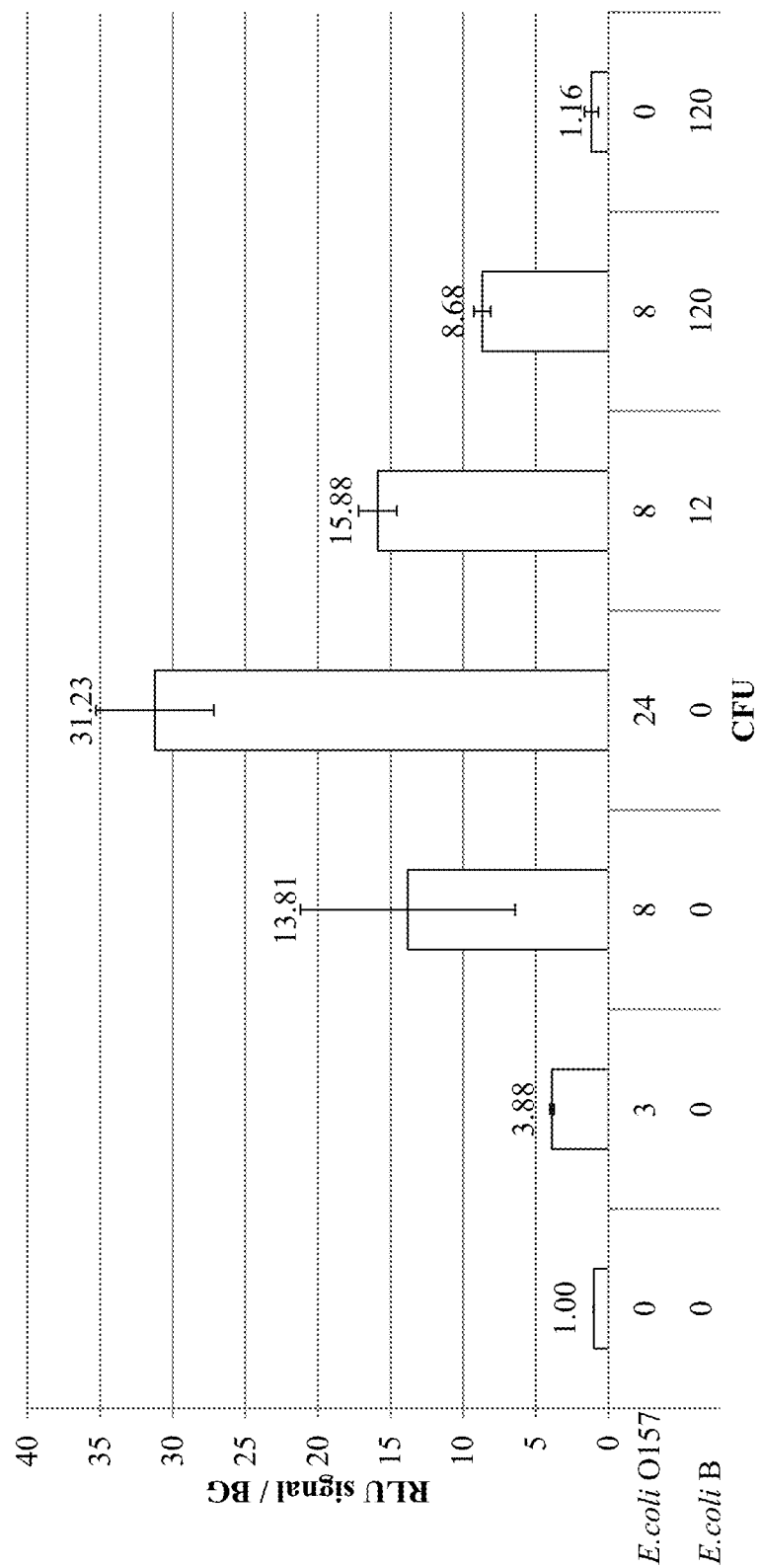
FIG. 4 demonstrates an embodiment of the invention showing detection of known numbers of E. coli O157:H7 cells in a sample that also contains E. coli B, using antibody specific for E. coli O157:H7 conjugated to HRP according to an embodiment of the invention. The number of E. coli O157:H7 cells or E. coli B cells is indicated as colony forming units (CFU) on the X-axis. The signal provided by the HRP-labeled antibody specific to E. coli O157:H7 cells using the substrate SIRIUS® is shown on the Y-axis as relative luminal units (RLU) over background (BG) signal (i.e., no cells) (RLU/BG). In this embodiment, the sample containing E. coli O157:H7 cells and/or E. coli B cells were incubated with the HRP-labeled antibody specific to E. coli O157:H7 cells and the complex then transferred to a filter plate.

In some embodiments, test samples containing more than one species of microorganism may be assayed. Some embodiments of the present invention enable quantitative detection of a specific microorganism despite the presence of other, non-target microorganisms. Thus, FIG. 4 demonstrates results for detection of *E. coli* O157:H7 in samples containing known numbers of *E. coli* O157:H7 with or without the additional presence of known numbers of *E. coli* B cells. In this embodiment, samples may first be incubated with anti-*E. coli* O157:H7 HRP-antibody conjugate (e.g., for ~1 hour) in a tube. The entire sample may then be applied to a PVDF filter plate and washed with PBST to remove unbound antibodies. The washed plate may then be placed in a luminometer where HRP chemiluminescence substrate may be injected. Readings may be taken immediately after injection, as well as at appropriate intervals thereafter. In FIG. 4, the X-axis shows the number of cells (CFU) in the sample, and signals measured over background are shown as relative luminal units (RLU) on the Y-axis. The example experiment demonstrates that affinity-purified, reverse-purified antibodies specific to *E. coli* O157:H7 detect *E. coli* O157:H7 in the presence of *E. coli* B in a test sample.

In some embodiments, the present invention comprises a size-based capture step before incubation with detection antibody. In such embodiments, incubation with detection antibody may be performed on a sample microorganism that is already captured on a filter. Thus, FIG. 5 demonstrates results for detection of *E. coli* O157:H7 where all steps were performed directly in a filter plate. In this embodiment, samples containing known numbers of *E. coli* O157:H7 cells are applied directly to PVDF filter plates. The sample solution may be removed by centrifugation or drawn through the filter by vacuum. Next anti-*E. coli* O157:H7 HRP-antibody may be added to the captured bacterial sample in a minimal volume and incubated (e.g., for ~1 hour). Wells may then be washed with PBST prior to being placed in a luminometer, where HRP chemiluminescence substrate may be injected into each well. Readings may be taken immediately after injection. This example experiment demonstrates that accurate detection of about 1, 2, 5, or 10 bacteria (CFU) is possible with a method that utilizes a single filter plate for all steps.

As noted herein, a variety of indicator moieties may be used. Some embodiments of the present invention utilize detection antibody conjugated to a reporter or indicator, such as luciferase. Thus, luciferase-conjugated detection antibody ("Luc-antibody") may be used in various methods according to the present invention. In some embodiments, the methods are very similar to those described above for HRP-antibody (e.g., FIGS. 3, 4 and 5), where the indicator reaction may be measured directly on the filter plate using a luminometer.

Luciferase-conjugated antibodies may not be commercially available, but preparation of such a conjugate may be achieved according to methods described herein. Briefly, antibody and luciferase may be conjugated by purification of the starting antibody, intermediate conjugation with Sulfo-SMCC to generate antibody-SMCC, desalting of the antibody-SMCC, and finally incubation with desalted recombinant luciferase. Details are provided in Example 5.

Figure 6:
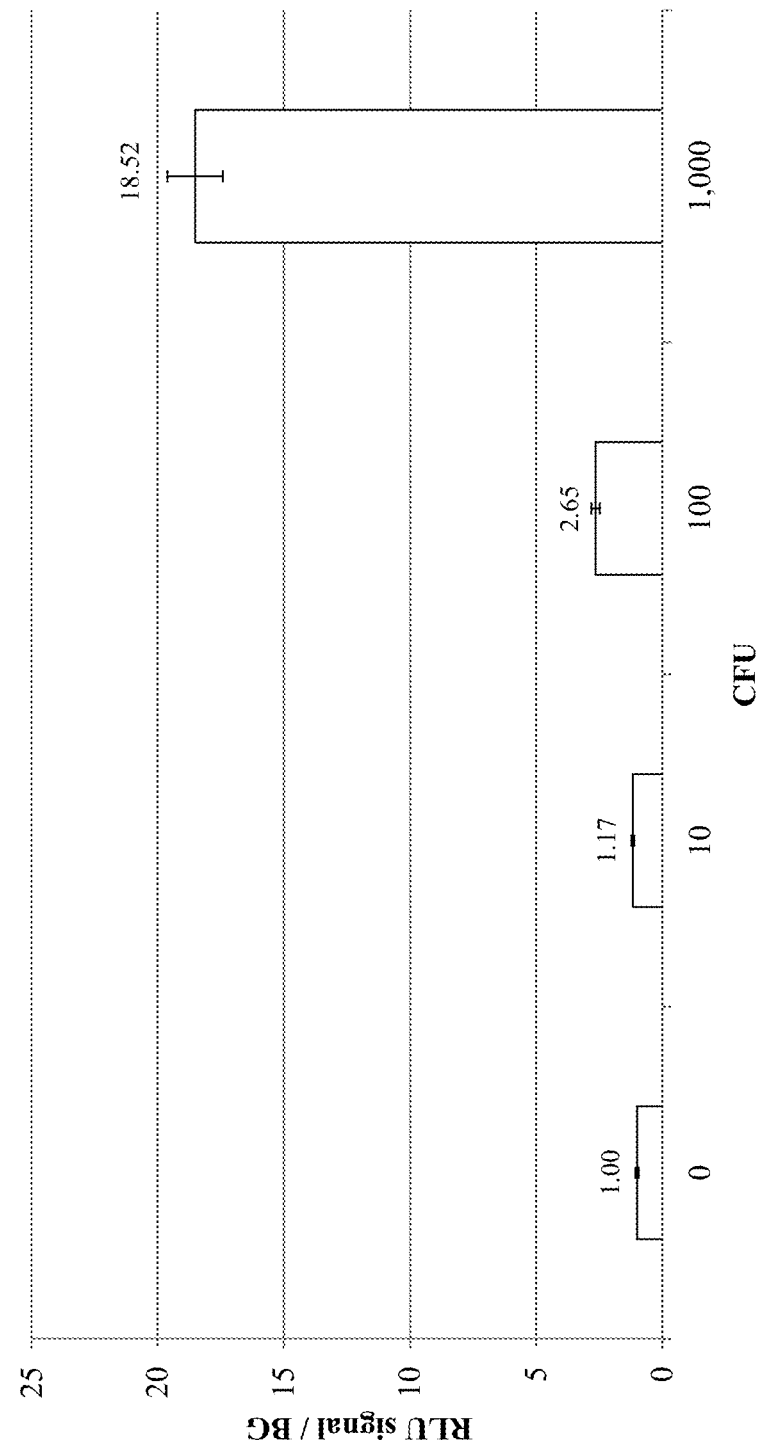
FIG. 6 demonstrates results for detection of E. coli O157:H7 in a sample, using antibody specific for E. coli O157:H7 conjugated to luciferase according to an embodiment of the invention. The number of E. coli O157:H7 cells is indicated as colony forming units on the X-axis. The signal provided by the luciferase-labeled antibody specific to E. coli O157:H7 cells is shown on the Y-axis as relative luminal units (RLU) over background (BG) signal (i.e., no cells) (RLU/BG). In this embodiment, the sample containing E. coli O157:H7 cells was transferred to a filter plate and then incubated with the HRP-labeled antibody specific to E. coli O157:H7 cells.

FIG. 6 demonstrates an example experiment for detection of *E. coli* O157:H7 using Luc-antibody. Similar to the embodiment depicted in FIG. 2, the sample may be captured by size-fractionation on filter plates as an initial step. Following incubation of the cells captured in plate wells with Luc-antibody, removal of unbound Luc-antibody, and washing, luciferin substrate reagent (or other luciferase substrate) may be added to wells and the reaction emissions may be measured in a luminometer. This example experiment demonstrates that increasing indicator signal using Luc-antibody corresponds to the increasing number of *E. coli* O157:H7 cells in the sample. Details are provided in Example 6.

ELISA Based Methods

As discussed herein, in some cases it may be preferred to capture the microorganism of interest on a solid surface (e.g., an assay well) prior to incubation with the detection binding agent.

Figure 7:
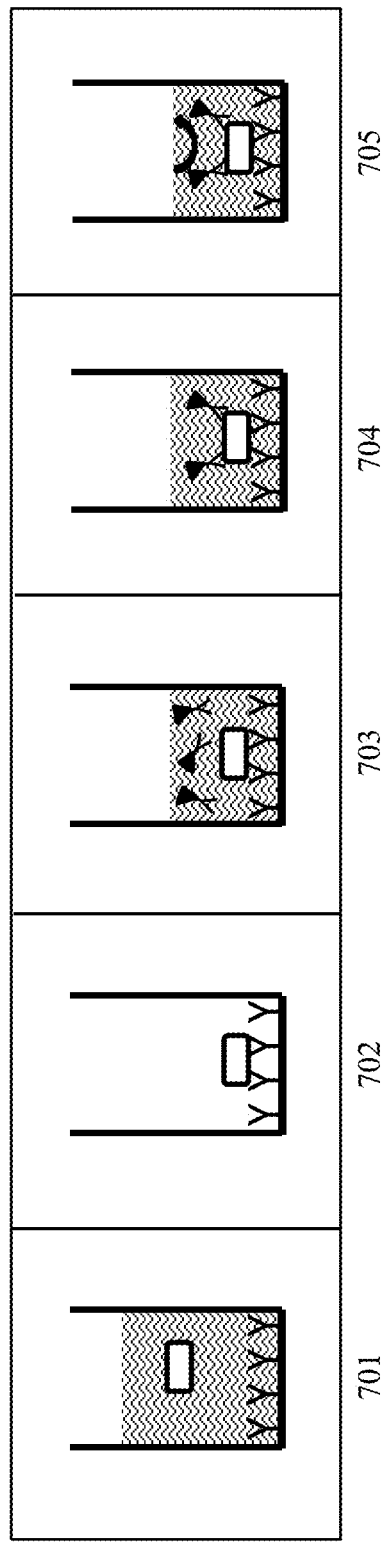
FIG. 7 illustrates an ELISA plate method for detection of a specific microorganism in a sample using free antibodies having a detectable moiety attached and a second antibody attached to a solid surface, according to certain embodiments of the invention. Both the free antibodies and the antibodies attached to the solid surface are specific for the microorganism of interest in the sample.

As seen in schematic FIG. 7, in one ELISA-based embodiment the sample is first applied to the microtiter plate well coated with bacterium-specific capture antibodies 701. The plate may be centrifuged to facilitate binding of the bacterium to the capture antibodies and some or all of the supernatant removed 702. Following sufficient time to allow for complete bacteria capture, a solution containing a reporter (e.g., HRP) conjugated bacterium-specific antibody is added to each sample 703. Incubation with the HRP-antibody conjugate results in the binding and attachment of antibodies to the captured bacterium 704. As discussed herein, there may be hundreds or thousands of molecules of an antibody specifically bound to epitopes on the bacterium. Finally, following several wash steps, the sample is incubated with the appropriate substrate (e.g., chemiluminescent substrate) and the reaction emission measured (e.g., in a luminometer) 705. The 'U'-shaped arrow in 705 represents the reaction of substrate with enzyme to generate indicator signal.

Figure 8:
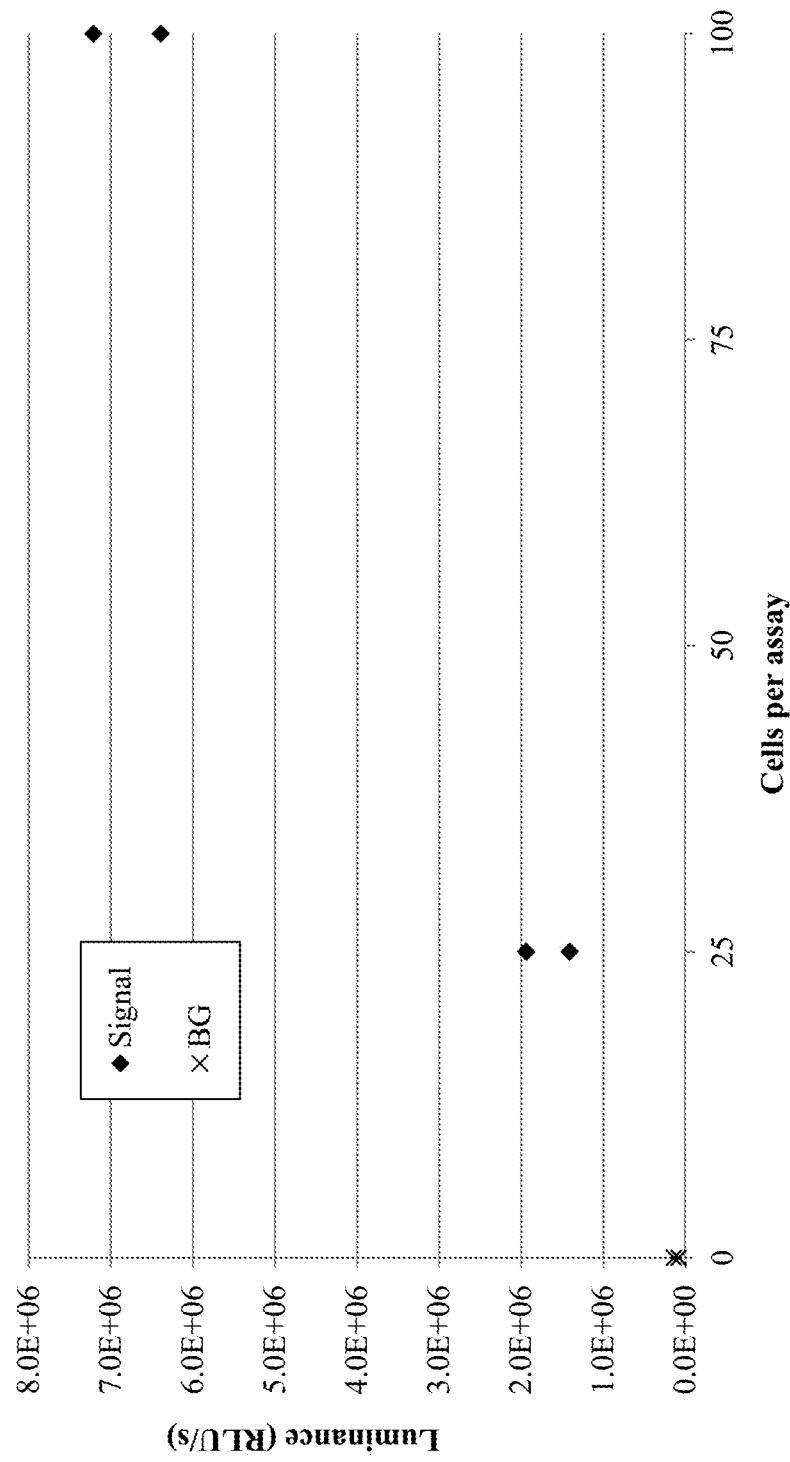
FIG. 8 demonstrates results for an ELISA-based experiment according to one embodiment of the invention. The number of E. coli O157:H7 cells is indicated on the X-axis. The signal provided by the HRP-labeled antibody specific to E. coli O157:H7 cells is shown on the Y-axis as relative luminal units (RLU) over the background signal (X) (i.e., no cells).
Figure 9:
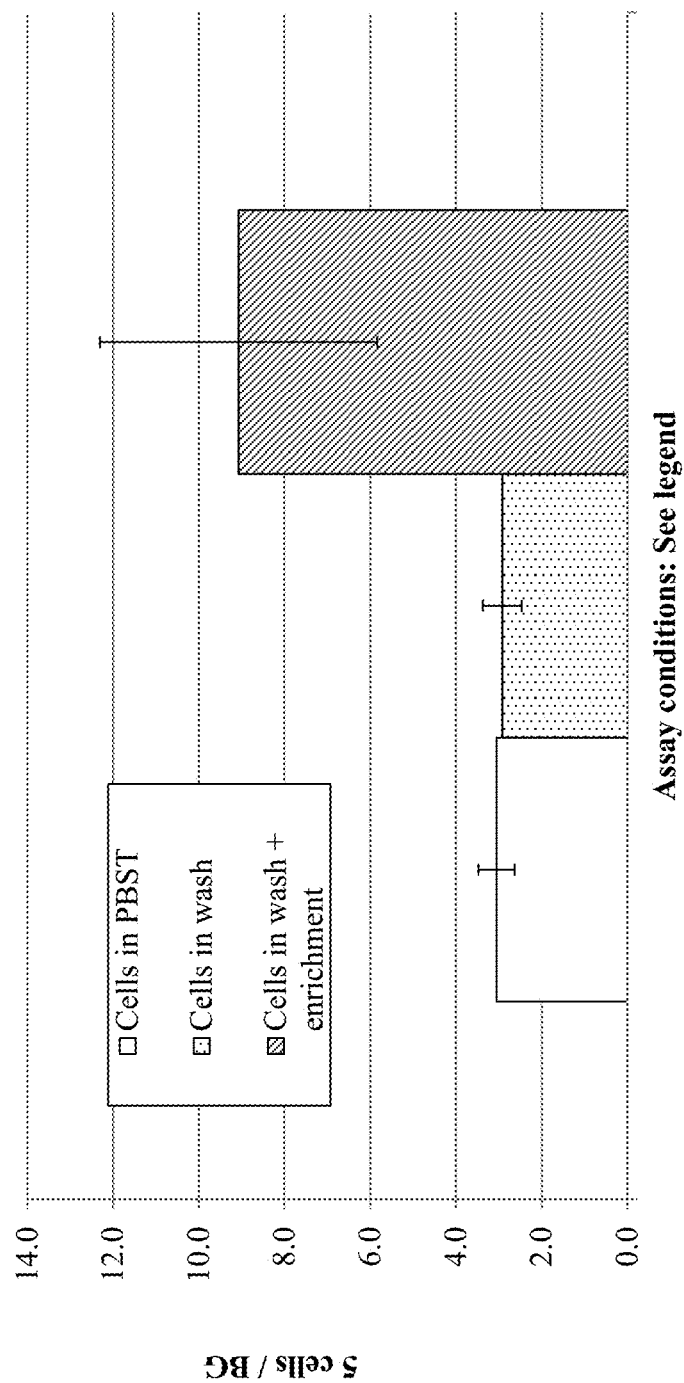
FIG. 9 demonstrates results for three different sample types: cells in PBST (Phosphate-buffered saline-Tween-20); cells in a spinach wash; and cells in an enriched spinach wash in an ELISA-based experiment according to an embodiment of the invention. The normalized signal from 5 cells over background for each sample type is shown on the Y-axis.

FIG. 8 shows results from an ELISA-based experiment as described in Example 7 and more generally illustrated in FIG. 7. Raw data are plotted from assays with 25 or 100 cells in PBST. The luminescence of 25 or 100 cells was clearly detected over background signal. FIG. 9 shows a comparison between assays using 5 cells in PBST, spinach wash, and wash with a brief enrichment time that may provide a 2- to 4-fold increase in cell number. The incubation time for enrichment in this experiment was 70-80 minutes. The signal from each type of sample is shown over background signal. Error bars indicate standard deviation. This experiment is described in detail in Example 9.

Figure 10:
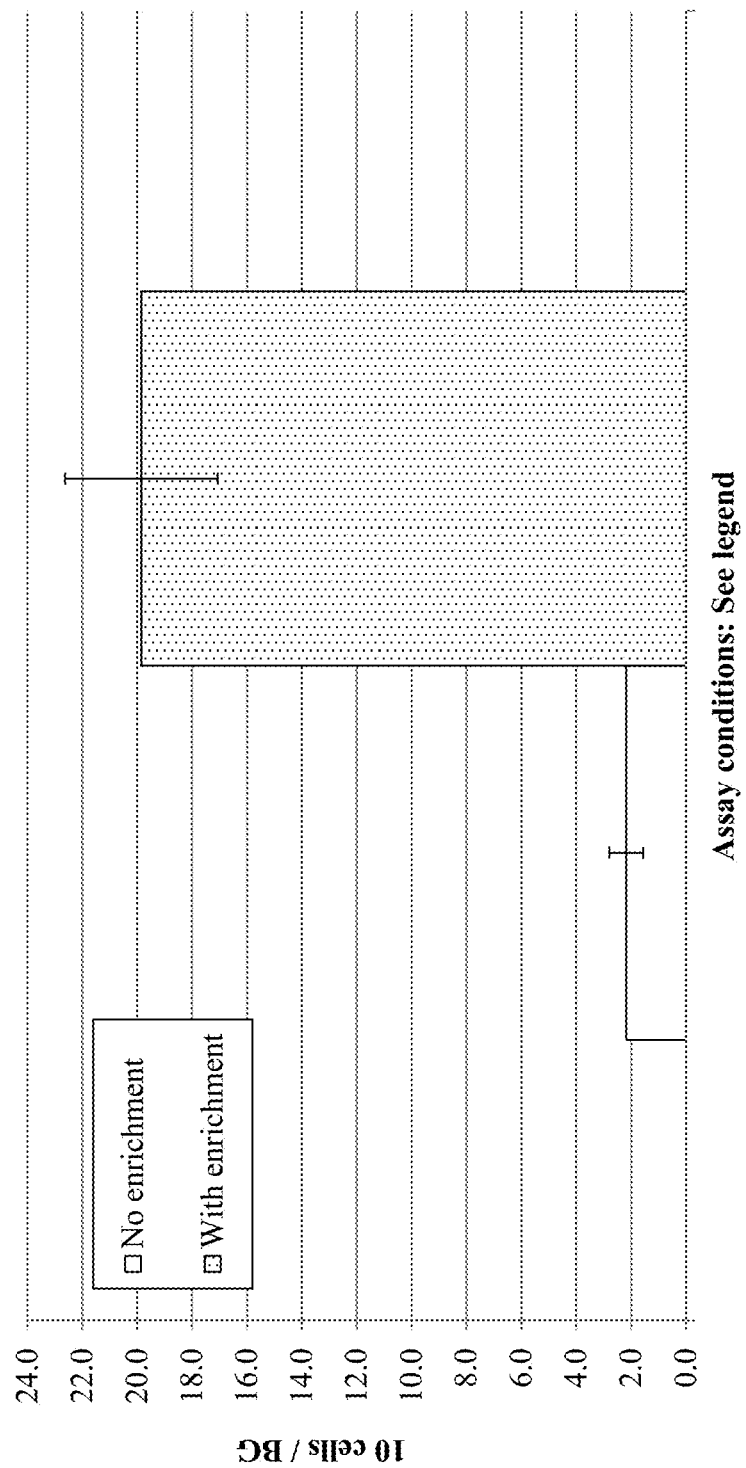
FIG. 10 demonstrates results for spinach wash samples with and without a brief enrichment according to alternative embodiments of the invention. The normalized signal from 10 cells over background for each sample type is shown on the Y-axis.

FIG. 10 shows results from an experiment where bacteria were directly spotted onto store-bought spinach leaves, allowed to dry, and then vegetable wash prepared, all as described in Example 10. In some experiments, a short (~1 hour) culturing for enrichment step is included. The capture and detection procedure are the same as previously described. The graph shows a comparison between spinach wash samples with and without a brief enrichment time. Each assay started with 10 cells, and the signal from each type of sample is shown over background signal and thus normalized to signal from 10 cells/background. This experiment is described in detail in Example 10.

Samples

Each of the embodiments of the methods and systems of the invention can allow for the rapid detection and quantification of microbes in a sample. For example, methods according to the present invention can be performed, most preferably, in about two hours or less.

Microbes detected by the methods and systems of the present invention include pathogens that are of commercial, medical or veterinary concern. Such pathogens include Gram-negative bacteria, Gram-positive bacteria, mycoplasmas and viruses. Any microbe for which a binding agent that is specific for the particular microbe has been identified can be detected by the methods of the present invention. Those skilled in the art will appreciate that there is no limit to the application of the present methods other than the availability of the necessary specific binding agent/microbe pairs.

Bacterial cells detectable by the present invention include, but are not limited to, bacterial cells that are food or water borne pathogens. Bacterial cells detectable by the present invention include, but are not limited to, all species of *Salmonella*, all strains of *Escherichia coli*, including, but not limited to *E. coli* O157:H7, all species of *Listeria*, including, but not limited to *L. monocytogenes*, and all species of *Campylobacter*. Bacterial cells detectable by the present invention include, but are not limited to, bacterial cells that are pathogens of medical or veterinary significance. Such pathogens include, but are not limited to, *Bacillus* spp., *Bordetella pertussis*, *Camplyobacter jejuni*, *Chlamydia pneumoniae*, *Clostridium perfringens*, *Enterobacter* spp., *Klebsiella pneumoniae*, *Mycoplasma pneumoniae*, *Salmonella typhi*, *Shigella sonnei*, *Staphylococcus aureus*, and *Streptococcus* spp.

The sample may be environmental or food or water samples and medical or veterinary samples. Samples may be liquid, solid, or semi-solid. Samples may be swabs of solid surfaces. Samples may include environmental materials, such as the water samples, or the filters from air samples or aerosol samples from cyclone collectors. Samples may be of meat, poultry, processed foods, milk, cheese, or other dairy products. Medical or veterinary samples include, but are not limited to, blood, sputum, cerebrospinal fluid, and fecal samples and different types of swabs.

Samples may be used directly in the detection methods of the present invention, without preparation or dilution. For example, liquid samples, including but not limited to, milk and juices, may be assayed directly. Samples may be diluted or suspended in solution, which may include, but is not limited to, a buffered solution or a bacterial culture medium. A sample that is a solid or semi-solid may be suspending in a liquid by mincing, mixing or macerating the solid in the liquid. A sample should also contain the appropriate concentrations of divalent and monovalent cations, including but not limited to $Na^+$, $Mg^{2+}$, and $K^+$. Preferably a sample is maintained at a temperature that maintains the viability of any pathogen cells contained within the sample. Such temperatures are at least about 25 degrees Celsius (C), more preferably no greater than about 45 degrees C., most preferably about 37 degrees C.

Systems and Kits of the Invention

In some embodiments, the invention comprises systems (e.g., automated systems or kits) comprising components for performing the methods disclosed herein. Some embodiments described herein are particularly suitable for automation or kits, given the minimal amount of reagents and materials required to perform the methods.

In some embodiments, the invention comprises a system for rapid detection of a microorganism of interest in a sample, comprising: a component for incubating the sample with a detection antibody specific for the microorganism of interest, wherein the detection antibody comprises an indicator moiety. The system may also include a component for capturing the microorganism from the sample on a solid support. The system may also include a component for washing the captured microorganism sample to remove unbound antibody. The system may also include a component for detecting the indicator moiety. In some embodiments, the system further comprises a component for determining an amount of the microorganism of interest in the sample, wherein the amount of indicator moiety detected corresponds to the amount of microorganism in the sample.

In some systems, the detection antibody is a free antibody that specifically recognizes and binds to the microorganism of interest. Thus in certain embodiments, the invention provides a system for rapid detection of a microorganism of interest in a sample, the system comprising: a component for incubating the sample with a detection antibody specific for the microorganism of interest, wherein the detection antibody comprises an indicator moiety; a component for capturing the microorganism from the sample on a solid support; a component for washing the captured microorganism sample to remove unbound antibody; a component for detecting the indicator moiety; and a component for determining amount of the microorganism of interest in the sample, wherein the amount of indicator moiety detected corresponds to the amount of microorganism in the sample. Such systems can include various embodiments and sub-embodiments analogous to those described above for methods of rapid detection of microorganisms.

In some system embodiments according to the invention, systems further comprise a component for determining an amount of the microorganism of interest in the sample, wherein the amount of indicator moiety detected corresponds to the amount of microorganism in the sample. In some embodiments, the system is automated, semi-automated, or controlled by the user via computer input. In some automated or semi-automated embodiments, at least one step is performed by a robot.

In some embodiments, the system is a kit. In such embodiments, each of the components of the system may be comprised in a self-contained unit that is deliverable from a first site to a second site. In some embodiments, the kit comprises at least a detection antibody specific for the microorganism of interest. The detection antibody may, in certain embodiments, be a free antibody that specifically recognizes and binds to the microorganism of interest. In some embodiments, the kit comprises a component for capturing a microorganism of interest and a component for detecting the microorganism. In some kit embodiments, the component for capturing is an ELISA plate coated with a capture antibody or a filter comprising a hydrophilic membrane which exhibits low protein binding capacity. Some kit embodiments further comprise a component for centrifuging.

For example, the system or kit may comprise a container comprising a reagent for incubating the sample with a detection antibody specific for the microorganism of interest, wherein the detection antibody comprises an indicator moiety. In an embodiment, the reagent may comprise an antibody specific to a microorganism of interest that is conjugated to an indicator moiety.

The system or kit may include at least one solid support for capturing the microorganism of interest. For example, in an embodiment, the system or kit may comprise a plurality of filters used to capture bacteria from a sample.

The system or kit may further comprise a component or components for detection of the indicator moiety. Thus, in certain embodiments, the system or kit may comprise a substrate used to generate a detectable product. Additionally or alternatively, the system or kit may comprise a luminometer for detection of a luminescent compound generated by the indicator moiety.

The system or kit may further comprise a binding agent attached to a solid surface for capturing the microorganism of interest from a sample. For example, the system or kit may comprise an antibody that binds to the microorganism of interest, wherein the antibody is coupled (i.e., covalently bound) to a solid support. The solid support may comprise a filter, or a bead or other solid supports known in the art or disclosed herein.

In some embodiments, the system or kit is automated, semi-automated, or controlled by the user via computer input. In some embodiments, the system or kit may comprise non-transient computer readable media designed for use with the systems and or methods of the invention. In certain embodiments, at least one step is performed by a robot.

The systems and kits of the invention include various components. As used herein, the term "component" is broadly defined and includes any suitable apparatus, composition, or collections of apparatuses or compositions suitable for carrying out the recited method. The components need not be integrally connected or situated with respect to each other in any particular way. The invention includes any suitable arrangements of the components with respect to each other. For example, the components need not even be in the same room. But in some embodiments, the components may be connected to each other in an integral unit. In some embodiments, the same components may perform multiple functions. For example, in various alternate embodiments, the components for various steps may be the same component or may be separate distinct components.

Computer Systems and Computer Readable Media

As noted herein, the system and kits, as described in the present technique or any of its components, may be embodied in a form for use with a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

In certain embodiments, the invention comprises non-transient computer readable media for use with a system of the invention. In other embodiments, the invention comprises non-transient computer readable media for use with a kit of the invention. In other embodiments, the invention comprises non-transient computer readable media for use with the various methods of the invention.

A computer system may comprise a computer, an input device, a display unit, and/or the Internet. The computer may further comprise a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit may allow the computer to connect to other databases and the Internet through an I/O interface. The communication unit allows the transfer to, as well as reception of data from, other databases. The communication unit may include a modem, an Ethernet card, or any similar device which enables the computer system to connect to databases and networks such as LAN, MAN, WAN and the Internet. The computer system may facilitate inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system may execute a set of instructions that are stored in one or more storage elements, in order to process input data. The storage elements may also hold data or other information as desired. The storage element may be in the form of an information source or a physical memory element present in the processing machine.

The environment may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices may also include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may comprise a single type of computer-readable medium such as random access memory (RAM). In other embodiments, the computing device may comprise two or more types of computer-readable medium such as random access memory (RAM), a disk drive, and cache. The computing device may be in communication with one or more external computer-readable mediums such as an external hard disk drive or an external DVD drive.

As discussed above, the embodiment may comprise a processor which is configured to execute computer-executable program instructions and/or to access information stored in memory. The instructions may comprise processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif.). In an embodiment, the computing device comprises a single processor. In other embodiments, the device comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device may comprise a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, the computing device may include a data store in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device is in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof.

Some of the embodiments of the technology described herein can be defined according to any of the following numbered paragraphs:

(1) A method for rapid detection of a microorganism of interest in a sample, comprising: capturing the microorganism from the sample on a solid support; incubating the microorganism sample with a detection antibody specific for the microorganism of interest, wherein the detection antibody comprises an indicator moiety; and detecting the indicator moiety, wherein positive detection of the indicator moiety indicates that the microorganism is present in the sample.

(2) The method of paragraph 1, wherein the detection antibody is a free antibody specific for surface antigens of the microorganism, and optionally wherein the solid support is a filter which captures the microorganism of interest based on size, and optionally wherein the filter comprises a hydrophilic membrane which exhibits low protein binding capacity.

(3) The method of paragraphs 1 or 2, wherein at least 60% of the detection antibody binding sites on the surface of the microorganism are bound to detection antibody following the incubating step, and/or wherein at least 100,000 detection antibodies are bound to the surface of a single cell of the microorganism, and/or wherein the method can detect as few as 10 cells of the microorganism in the sample, and/or wherein the total time required for detection is less than 2.5 hours.

(4) The method of any of paragraphs 1-3, wherein the indicator moiety is an enzyme, which is optionally horseradish peroxidase or luciferase; and wherein incubation with a reactive substrate produces a detectable signal which corresponds to the amount of enzyme present; and optionally further comprising washing the captured microorganism sample to remove unbound antibody.

(5) The method of any of paragraphs 1-4, wherein the capturing step further comprises binding microorganism with a capture antibody; optionally wherein a moiety conjugated to the capture antibody facilitates binding of the microorganism to a solid support; and optionally wherein the ELISA plate is first coated with capture antibody, and then the sample is applied to the ELISA plate; and optionally wherein the ELISA plate further comprises a white or colored background or a combination of white and colored background.

(6) The method of any of paragraphs 1-5, wherein the incubating step further comprises addition of an excess of non-specific non-labeled blocking antibody derived from the same species as the detection antibody; and optionally wherein the capture antibody and/or the detection antibody is affinity-purified and/or reverse-purified.

(7) The method of any of paragraphs 1-6, further comprising a centrifuging step and/or a high-salt washing step, and wherein the microorganism comprises at least one of a bacterium, or a fungus, or a yeast, or a virus.

(8) A system for rapid detection of a microorganism of interest in a sample, comprising: a component for incubating the sample with a detection antibody specific for the microorganism of interest, wherein the detection antibody comprises an indicator moiety; a component for capturing the microorganism from the sample on a solid support; a component for washing the captured microorganism sample to remove unbound antibody; and a component for detecting the indicator moiety.

(9) The system of paragraph 8, wherein the system further comprises a component for determining an amount of the microorganism of interest in the sample, wherein the amount of indicator moiety detected corresponds to the amount of microorganism in the sample; and optionally wherein the detection antibody is a free antibody.

(10) The system of paragraphs 8 or 9, wherein the system is automated, semi-automated, or controlled by the user via computer input; and optionally wherein at least one step is performed by a robot.

(11) The system of any of paragraphs 8-10, wherein the system is a kit, wherein the kit optionally comprises a component for capturing a microorganism of interest and a component for detecting the microorganism; and wherein the kit optionally comprises free antibody.

(12) The system of any of paragraphs 8-11, wherein the component for capturing is an ELISA plate coated with a capture antibody or a filter comprising a hydrophilic membrane which exhibits low protein binding capacity.

(13) The system of any of paragraphs 8-12, further comprising a component for centrifuging.

(14) A kit for rapid detection of a microorganism of interest in a sample, comprising free antibodies specific for the microorganism of interest, optionally further comprising an ELISA plate, a filter plate, and/or a high-salt wash.

(15) Computer readable media designed for use with any of the methods or systems of paragraphs 1-14.

EXAMPLES

Example 1. Specific and Quantitative Capture of *E. coli* O157:H7 Using Antibodies and Beads FIG. 1 depicts an example experiment demonstrating that antibodies against *E. coli* O157:H7, used in conjunction with magnetic streptavidin-coated beads, captured *E. coli* O157:H7 specifically and quantitatively from samples, but did not capture *E. coli* B or *Salmonella typhimurium*. In order to demonstrate specificity in capturing intact, viable bacterial cells from solution, polyclonal antibodies to surface epitopes of *E. coli* O157:H7 were obtained from KPL (affinity-purified and reverse-purified to minimize cross-reactivity).

Cultures of both *E. coli* strains and *S. typhimurium* were grown in LB broth, harvested, and washed with phosphate buffer (1.1 mM $KH_2PO_4$, 5.6 mM $Na_2HPO_4$, 154 mM NaCl, pH 7.4). The washed cells were then counted and diluted to a concentration between 5-20 cells per mL.

A sample containing *E. coli* O157:H7 was combined with a solution containing BSA and biotin-conjugated antibody. Approximately 10 ng biotinylated, polyclonal anti-*E. coli* antibody (equivalent to about $4 \times 10^{10}$ antibody molecules) produced by KPL was added to each of the cell suspensions. A control experiment, where antibody was not added to the cell suspension, was also performed in parallel. The BSA concentration was ~1%, and the total biotin-antibody was 10 ng. The mixture was rotated end-over-end for 1 hour.

Following incubation with antibodies, $4 \times 10^7$ streptavidin-coated magnetic microparticles (Invitrogen/Life Technologies) were added to the mixture and incubated a further 30 minutes. The cell-antibody-bead complexes were then collected using a magnetic stand, and the unbound fraction (supernatant) was removed. The beads were gently washed with phosphate buffer containing Tween-20 (1.1 mM $KH_2PO_4$, 5.6 mM $Na_2HPO_4$, 154 mM NaCl, pH 7.4, 0.05% Tween-20). Both the supernatants and captured cell-bead complexes were then spread onto LB agar plates and the plates incubated overnight at 37° C. to determine CFU. Capture of *E. coli* O157:H7 with anti-O157:H7 antibodies, but not *E. coli* B or *Salmonella typhimurium*, was specific and quantitative (FIG. 1).

Example 2. Detection of *E. coli* O157:H7 Using HRP-Ab Added to Solution Before Capture

*E. coli* O157:H7 was grown in Luria-Bertani (LB) broth. Cell concentrations were determined using a hemocytometer. Cells were diluted to approximately 3, 9, and 27 cells in 300 μL 1% BSA/PBST (PBST is Phosphate-buffered saline-Tween-20). The actual cell count (CFU) was determined by plating 100 μL of the "27 cells/300 μL" sample. Ten nanograms (10 ng) of HRP-conjugated, anti-*E. coli* O157:H7 antibody (KPL catalog #04-95-90, goat polyclonal, affinity-purified and reverse-purified antibody) in 10 μL 1% BSA/PBST was then added to each sample. Samples were mixed by rotating the tubes end-over-end for 1.5 hours at room temperature. The mixture was then transferred directly to 0.45 μm, hydrophilic-PVDF filter plates (Whatman catalog #7700-3306) that had been pre-blocked with 1% BSA/PBST. The sample solution was removed by centrifugation. After the sample had been applied to the filter membrane, the wells were washed 6 times with 300 μL PBST. The washed plate was then placed in a luminometer (Promega GLOMAX® 96) where 100 μL HRP chemiluminescent substrate (Advansta SIRIUS® substrate, catalog # K-12043-D10) was added to each well. Sample readings were taken immediately after injection. FIG. 3 demonstrates results from an example experiment. The experiment was performed in duplicate with the average and standard deviation plotted. The X-axis shows the number of cells (CFU) in the sample, and indicator signals measured are shown as relative luminal units (RLU) on the Y-axis. Indicator signal is shown as fold increase over the zero cell samples. This example experiment shows detection of about 5, 14, and 42 CFU from 300 μL sample using 10 ng HRP-antibody.

Example 3. Detection of *E. coli* O157:H7 in the Presence of *E. coli* B

*E. coli* O157:H7 and *E. coli* B were grown in LB broth. Cell concentrations were determined using a hemocytometer. *E. coli* O157:H7 was diluted to approximately 3, 9, and 27 cells in 50 μL 1% BSA/PBST. *E. coli* B was diluted to approximately 15 and 150 cells in 50 μL 1% BSA/PBST. The actual cell count (CFU) was determined by plating 50 μL of the cell dilutions. Mixtures of *E. coli* O157:H7 and *E. coli* B were made by combining 50 μL of the cell dilutions or adding 50 μL 1% BSA/PBST (for 100 μL total starting sample). Ten nanograms (10 ng) of HRP-conjugated, anti-*E. coli* O157:H7 antibody (KPL catalog #04-95-90) in 10 μL 1% BSA/PBST was then added to each sample. Samples were mixed by rotating the tubes end-over-end for 1.5 hours at room temperature. The mixture was then transferred directly to 0.45 μm, hydrophilic-PVDF filter plates (Whatman catalog #7700-3306) that had been pre-blocked with 1% BSA/PBST. The sample solution was removed by centrifugation. After the sample had been applied to the filter membrane, the wells were washed 6 times with 300 μL PBST. The washed plate was then placed in a luminometer (Promega GLOMAX® 96) where 100 μL HRP chemiluminescent substrate (Advansta SIRIUS® substrate, catalog # K-12043-D10) was added to each well. Sample readings were taken immediately after injection.

FIG. 4 demonstrates results from an example experiment. The experiment was performed in duplicate with the average and standard deviation of the RLU signal over background plotted. The X-axis shows the number of cells (CFU) in the sample, and indicator signals measured are shown as relative luminal units (RLU) on the Y-axis. Signal is shown as fold increase over the zero cell samples. This example experiment shows 3, 8, and 24 CFU of *E. coli* O157:H7 were specifically detected in samples, but *E. coli* B was not detected. *E. coli* O157:H7 was detected in the presence of *E. coli* B without interference, even where the ratio of *E. coli* B to *E. coli* O157:H7 cells was 120:8.

Example 4. *E. coli* O157:H7 Detection with all Steps Performed in a Filter Plate

Figure 5:
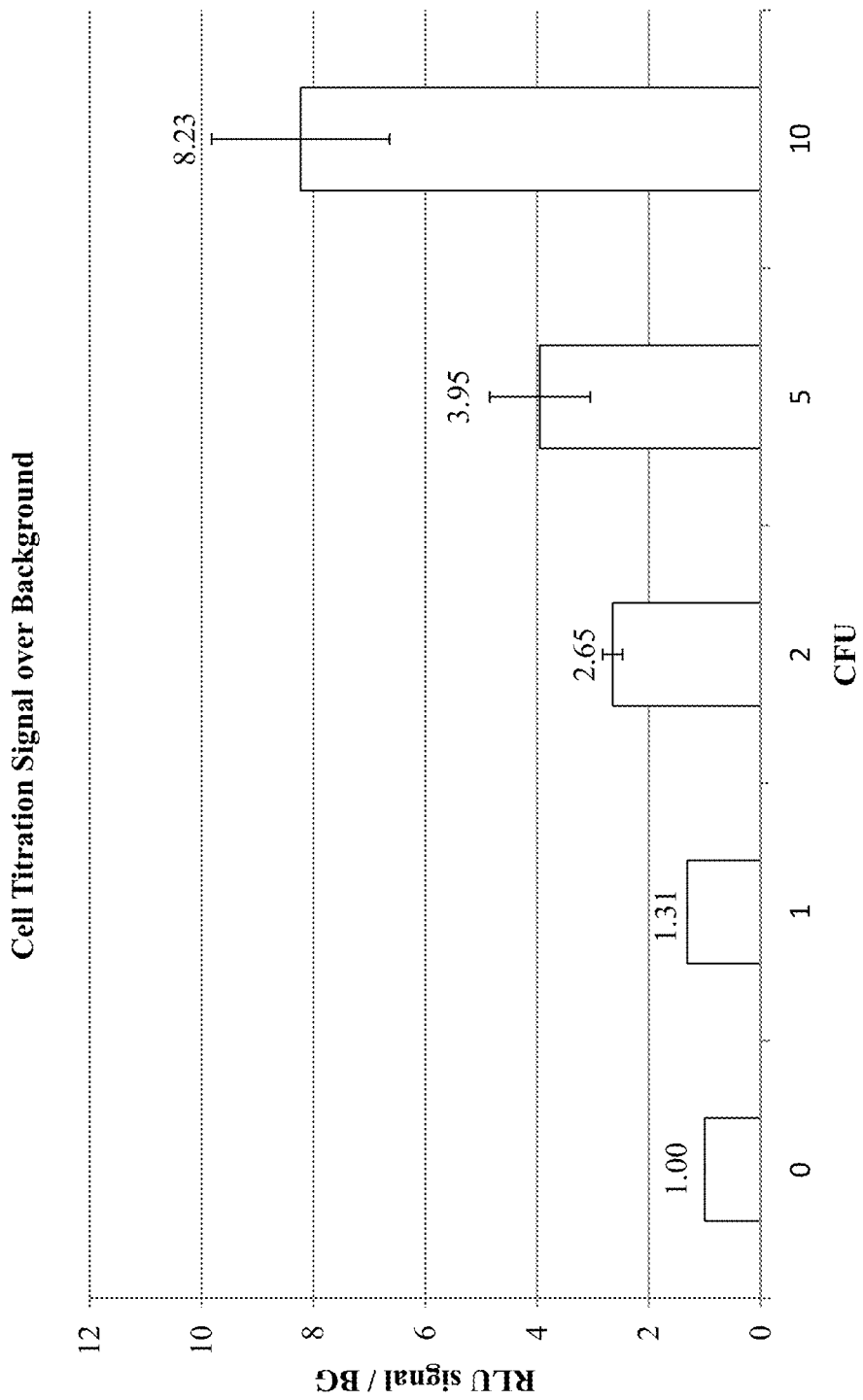
FIG. 5 demonstrates results for detection of E. coli O157:H7 in a sample, using antibody specific for E. coli O157:H7 conjugated to HRP according to an embodiment of the invention. In this embodiment, samples containing the E. coli O157:H7 cells were incubated with the HRP-labeled antibody specific to E. coli O157:H7 cells on a filter plate. The number of E. coli O157:H7 cells is indicated as colony forming units (CFU) on the X-axis. The signal provided by the HRP-labeled antibody specific to E. coli O157:H7 cells is shown on the Y-axis as relative luminal units (RLU) over background (BG) signal (i.e., no cells) (RLU/BG). In this embodiment, the sample containing E. coli O157:H7 cells was transferred to a filter plate and then incubated with the HRP-labeled antibody specific to E. coli O157:H7 cells.

*E. coli* O157:H7 was grown in LB broth. Cell concentrations were determined using a hemocytometer. Cells were diluted to approximately 1, 2, 5, and 10 cells in 300 μL 1% BSA/PBST. Cell count was confirmed by plating the cell dilutions (CFU assay). The entire sample was applied to 0.45 μm, hydrophilic-PVDF filter plates (Whatman catalog #7700-3306) that had been pre-blocked with 1% BSA/PBST. The sample solution was removed by centrifugation. Ten nanograms (10 ng) of HRP-conjugated, anti-*E. coli* O157:H7 antibody (KPL catalog #04-95-90) in 50 μL 1% BSA/PBST was then added to each sample and the samples incubated with shaking for 1.5 hours at room temperature. The antibody-HRP solution was removed by centrifugation and each well was washed 6 times with 300 μL PBST. The washed plate was then placed in a luminometer (Promega GLOMAX® 96) where 100 μL it HRP chemiluminescent substrate (Advansta SIRIUS® substrate, catalog # K-12043-D10) was added to each well. Sample readings were taken immediately after injection. FIG. 5 illustrates results from an example experiment. The experiment was performed in duplicate with the average and standard deviation of the RLU signal over background plotted. The X-axis shows the number of cells (CFU) in the sample, and indicator signals measured are shown as relative luminal units (RLU) on the Y-axis. Signal is shown as fold increase over the zero cell samples. This example experiment shows detection of a single CFU (as well as 2, 5, and 10 CFU) from a total starting sample volume of 300 µL, where the entire assay was performed in a single filter plate.

Example 5. Production of Antibody-Luciferase Conjugate

Antibodies to be used in a conjugation reaction were purified using a size-exclusion chromatography (SEC) column to remove aggregates. One milligram (1 mg) antibody was run on a Tosoh Bioscience TSKgel® G3000SW (Catalog #05789, 7.5 mm IDx30 cm length) on a Beckman Coulter SYSTEM GOLD® HPLC system. The system was run in phosphate-buffered saline (PBS) at a rate of 1 mL/min. Fractions corresponding to antibody monomers were collected and the antibody concentration determined using a NANODROP® spectrophotometer.

Fifty micrograms (50 µg) purified antibody in PBS was incubated with 7.5-9 µg Sulfo-SMCC (Thermo Scientific #22322) in water at for 1 hour at room temperature. The antibody-SMCC conjugate was then desalted using Thermo Scientific Zeba spin columns (#89882) to remove unreacted Sulfo-SMCC.

Recombinant luciferase (Promega, QUANTILUM® Luciferase, # E1701) was prepared by diluting to 1 mg/mL in PBS prior to desalting on Zeba columns.

Conjugation of antibody and luciferase was performed by incubating 20 µg desalted antibody with either 20 or 40 µg desalted luciferase. Reactions were mixed and incubated overnight at room temperature.

Antibody-luciferase conjugates were purified using the SEC column/HPLC system as described above. Fractions corresponding to the conjugate were collected and concentrated using spin concentrators (Millipore AMICON® Ultra # UFC500308). The conjugate was stabilized by adding BSA to 1 mg/mL prior to storage at 4° C. This antibody-luciferase conjugate was used in the experiment described in Example 6.

Example 6. Detection of *E. coli* O157:H7 with Antibody-Luciferase Conjugate Samples containing a known number of bacterial cells in 300 µL PBS/BSA buffer were added to a 96-well PVDF-filter plate (0.45 µm pore, Whatman #7700-3306). The sample liquid was removed either by centrifugation or vacuum. One microliter (1 µL) concentrated antibody-luciferase reagent diluted to 50 µL in PBS/BSA was added to each well and incubated for at least 1 hour at room temperature. The antibody-luciferase reagent was removed by vacuum and the wells were washed 6 times with 300 µL PBST. Fifty microliters (50 µL) luciferase substrate (Promega # E1501) was added to each well and reactions were read in a Promega 96-well luminometer (Promega GLOMAX® 96). FIG. 6 demonstrates results for an example experiment using antibody-luciferase conjugate to detect *E. coli* O157:H7. The X-axis shows the number of cells (CFU) in the sample, and indicator signals measured are shown as relative luminal units (RLU) on the Y-axis. This example experiment shows that 10, 100, and 1,000 CFU bacterial cells were detected.

Example 7. ELISA-Based Method

In experiments using an ELISA-based method, a white 96-well ELISA plate was coated with 300 ng monoclonal antibody (in 100 µL PBS) specific to the bacterium of interest at room temperature for 2-3 hours. Wells were washed with PBS (200 µLx3 washes), blocked with 5% BSA/PBS (300 µL) at room temperature for 1-1.5 hours, and again washed with 300 µL PBSx1. Test samples (300 µL) were applied to the wells.

The ELISA plate was centrifuged at 700xg for 30 minutes and then incubated at room temperature for 0.5-1 hour. Wells were washed with PBST (127 mM NaCl, 0.05% Tween20), (300 µLx2 washes); high-salt PBST (287 mM NaCl, 0.5% Tween20), (300 µLx1 wash); and again with PBST (127 mM NaCl, 0.05% Tween20), (300 µLx1 wash).

Samples were then incubated with 10 ng polyclonal antibody-HRP specific for the target bacterium and 500 ng whole goat IgG antibody in 100 µL 1% BSA/PBST, at room temperature for 1 hour, with shaking.

Wells were again washed with PBST (127 mM NaCl, 0.05% Tween20), (200 µLx2 washes, followed by 300 µLx1 wash); high-salt PBST (287 mM NaCl, 0.5% Tween20), (300 µLx2 washes); and PBST (127 mM NaCl, 0.05% Tween20), (300 µLx1 wash). Finally, Western SIRIUS® substrate was added to each well and the luminescence was measured in a luminometer.

Example 8. *E. coli* O157:H7 Detection in an ELISA-Based Method

*E. coli* O157:H7 was grown in LB broth. Cell concentrations were calculated using a hemocytometer. Cells were diluted to approximately 25 and 100 cells in 300 µL PBST. Cell count was confirmed by plating the cell dilutions (CFU assay). The entire sample was applied to a white, luminometer microtiter plate (Greiner Bio-one, Lumi600) pre-coated with 300 ng anti-*E. coli* O157:H7 monoclonal antibody (Abeam ab156617) and blocked with 5% BSA/PBS. The microtiter plate was then centrifuged at 700xg for 30 min and incubated a further 0.5-1 hour at room temperature. Ten nanograms (10 ng) of HRP-conjugated, anti-*E. coli* O157:H7 antibody (KPL catalog #04-95-90) and 500 ng whole goat IgG antibody (Thermo Scientific #31245) in 100 µL 1% BSA/PBST was then added to each sample and the samples incubated with shaking for 1 hour at room temperature. The washed plate was then placed in a luminometer (Promega GLOMAX® 96) where 100 µL HRP chemiluminescent substrate (Advansta SIRIUS® substrate, catalog # K-12043-D10) was added to each well. Sample readings were taken immediately after injection. The results of this experiment are shown in FIG. 8.

Example 9. *E. coli* O157:H7 Detection in a Food Sample Using an ELISA-Based Method This experiment used the same assay and procedure as Example 8 above, except the *E. coli* cells were diluted directly into vegetable wash instead of PBST.

To prepare the vegetable wash, vegetable leaves (e.g., spinach or lettuce) were weighed and added to a clean plastic bag. One mL of LB (+/−0.01-0.05% Tween20) was added per each gram (g) of vegetable. Leaves and solution were mixed manually for a few minutes. Liquid was then extracted from the plastic bag and used as the "vegetable wash." Using this method, ~1 million bacteria were found to reside on a single spinach leaf (1-2 g).

Based on this method of vegetable wash preparation, approximately $1 \times 10^6$ bacteria are present per mL of wash. Thus in a sample volume of 300 µL there are approximately 300,000-350,000 non-target bacteria. In some cases, a short (~1 hour) enrichment step is included. The results of this experiment are shown in FIG. 9.

Example 10. Detection of *E. coli* O157:H7 Washed Off a Food Sample Using an ELISA-Based Method This experiment used the same assay and procedure as Examples 8 and 9 above, except that to further evaluate the ability to detect *E. coli* O157:H7 in a more realistic situation, known cell numbers were dried onto vegetable leaves and then washed off for testing.

First, a PBS solution was prepared containing a known concentration of *E. coli* O157:H7. To spot the bacteria, 10 µL of the solution was pipetted onto the surface of a vegetable leaf. The leaf and spotted solution was allowed to dry in a sterile hood for approximately 30 minutes or until dry. The vegetable wash was then prepared from the spotted vegetables.

To prepare the vegetable wash, vegetable leaves (e.g., spinach or lettuce) were weighed and added to a clean plastic bag. One mL of LB (+/−0.01-0.05% Tween20) was added per each gram (g) of vegetable. Leaves and solution were mixed manually for a few minutes. Liquid was then extracted from the plastic bag and used as the "vegetable wash." Using this method, ~1 million bacteria were found to reside on a single spinach leaf (1-2 g). The results of this experiment are shown in FIG. 10.

We claim:

1. A method for detection of a microorganism of interest in a sample, comprising:
   capturing the microorganism, if present, from the sample on a solid support, wherein the solid support is a filter that captures the microorganism based on a size of the microorganism, wherein the filter comprises a hydrophilic polyvinylidene difluoride (PVDF) membrane and the sample is applied to the solid support by a centrifugation;
   incubating the microorganism from the sample with a detection antibody specific for surface antigens of the microorganism, wherein the detection antibody comprises an indicator moiety; and
   detecting the indicator moiety, wherein positive detection of the indicator moiety indicates that the microorganism is present in the sample.

2. The method of claim 1, further comprising washing the captured microorganism sample to remove unbound antibody.

3. The method of claim 1, wherein the detection antibody specific for the microorganism is a free antibody and is specific for surface antigens of the microorganism.

4. The method of claim 1, wherein at least 100,000 molecules of detection antibodies are bound to the surface of a single cell of the microorganism.

5. The method of claim 1, wherein the method can detect as few as 1-3 cells of the microorganism in the sample.

6. The method of claim 1, wherein the total time required for detection is less than 2 hours.

7. The method of claim 1, further comprising a washing step with a wash comprising greater than 0.25 M NaCl or greater than 0.25% Tween 20.

8. The method of claim 7, wherein the indicator moiety is an enzyme.

9. The method of claim 8, wherein the enzyme is horseradish peroxidase or luciferase.

10. The method of claim 9, wherein incubation with a reactive substrate produces a detectable signal which corresponds to the amount of enzyme present.

11. The method of claim 1, wherein the incubating step further comprises addition of an excess of non-specific non-labeled blocking antibody derived from the same species as the detection antibody.

12. The method of claim 1, wherein the detection antibody is affinity-purified and/or reverse-purified.

13. The method of claim 1, wherein the microorganism comprises at least one of a bacterium, or a fungus, or a yeast.

14. The method of claim 7, wherein the wash comprises greater than 0.25 M NaCl and greater than 0.25% Tween 20.

15. The method of claim 1, wherein the capturing the microorganism is by applying the sample directly to the filter by centrifuge or vacuum.

16. The method of claim 1, wherein at least 10,000 molecules of antibodies are bound to the surface of a single microorganism cell.

* * * * *